United States Patent [19]

Abe et al.

[11] Patent Number: 5,385,942
[45] Date of Patent: Jan. 31, 1995

[54] QUINONE DERIVATIVES AND PHARMACOLOGICAL USE

[75] Inventors: Shinya Abe; Yasushi Okamoto; Katsuya Tagami; Shigeki Hibi; Junichi Nagakawa; Kazuo Hirota; Ieharu Hishinuma; Kaname Miyamoto; Takashi Yamanaka; Hiromitsu Yokohama; Tsutomu Yoshimura; Tohru Horie; Yasunori Akita; Koichi Katayama; Isao Yamatsu, all of Ibaraki, Japan

[73] Assignee: Eisai Co., Ltd., Tokyo, Japan

[21] Appl. No.: 22,688

[22] Filed: Mar. 1, 1993

Related U.S. Application Data

[62] Division of Ser. No. 576,054, Aug. 31, 1990, Pat. No. 5,210,239.

[30] Foreign Application Priority Data

Sep. 11, 1989 [JP] Japan .................. 1-232761

[51] Int. Cl.$^6$ .................. A61K 31/19; C07D 265/30
[52] U.S. Cl. .................. 514/568; 514/579; 514/646; 514/716; 514/718; 514/728; 514/734; 544/176; 544/386; 546/194; 548/195; 548/204; 549/80; 549/427; 560/142; 560/144; 568/587; 568/654; 568/705; 568/807; 568/811; 568/813

[58] Field of Search .................. 568/587, 654, 705, 807, 568/811, 813; 560/142, 144; 514/568, 579, 646, 716, 718, 728, 734; 544/386, 176; 546/194; 548/204, 195; 549/80, 427

[56] References Cited

U.S. PATENT DOCUMENTS 5,169,856 12/1992 Goto et al. .................. 514/331
5,286,750 2/1994 Mueller et al. .................. 514/546

*Primary Examiner*—Johann Richter
*Assistant Examiner*—Kimberly J. Kestler
*Attorney, Agent, or Firm*—Flynn, Thiel, Boutell & Tanis

[57] ABSTRACT

A quinone derivative useful in the treatment of hepatic diseases defined by the general formula:

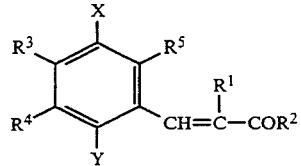

where X and Y may be the same or different from each other and are each a hydroxyl group, a group represented by the formula $-(-OCH_2-)_n-OR^6$, wherein n is 0 or 1 and $R^6$ is a lower alkyl group, or an acyl group.

19 Claims, No Drawings

QUINONE DERIVATIVES AND PHARMACOLOGICAL USE

This is a division of Ser. No. 7/576 054, filed Aug. 31, 1990 now U.S. Pat. No. 5,210,239.

FIELD OF INDUSTRIAL APPLICATION

The present invention relates to a benzoquinone derivative which exhibits an excellent activity as a medicine.

More particularly, the present invention is concerned with a novel benzoquinone derivative useful as a therapeutic agent for hepatic diseases.

BACKGROUND OF THE INVENTION AND PRIOR ART

Since the cause, image and pathophysiology of different hepatic diseases are varied and involve numerous unknown factors, the present status is that it is very difficult to develop a therapeutic agent for these diseases.

At the present time, representative examples of medicines widely used for treating and preventing hepatic diseases and which are clinically appreciated include glycyrrhizin preparations. Although they are believed to be effective against hepatic disorders, cirrhosis or hepatitis and for the postoperative protection of the liver, etc., their efficacy is not so strong and, what is worse they exhibit steroidal side effects. Further, they are available in the form of an intravenous injection and are disadvantageously inactive when orally administered.

Accordingly, it has been eagerly desired to develop a medicine which is highly safe and will exhibit its effect even when orally administered.

Under the above-described circumstances, the present inventors have started exploratory researches with a view to developing a therapeutic agent for hepatic diseases.

As a result, they have found that the benzoquinone derivative which will be described hereinbelow will attain the object of the present invention.

Examples of the benzoquinone derivatives which a pharmaceutical activity include those described in, e.g., Japanese Patent Laid-Open Nos. 223150/1987, 223150/1987 and 177934/1983.

The benzoquinone derivative disclosed in the Japanese Patent Laid-Open No. 223150/1987 is different from the compound (I) of the present invention in chemical structure and is believed to have an antiasthmatic activity, thus being different from the compound of the present invention also in its pharmaceutical activity.

Japanese Patent Laid-Open No. 177934/1983 discloses a benzoquinone derivative which is different from the compound of-the present invention in both efficacy and chemical structure.

Japanese Patent Laid-Open No. 185921/1988 discloses a therapeutic agent for hepatic diseases which is different from the compound of the present invention in chemical structure.

DETAILED DESCRIPTION OF THE INVENTION

The present invention relates to a benzoquinone derivative represented by the following general formula (I) and pharmacologically acceptable salts thereof:

$$A-CH=\overset{R^1}{\underset{|}{C}}-COR^2 \qquad (I)$$

wherein A is a group represented by the formula:

[benzoquinone structure with $R^3$, $R^4$, $R^5$ substituents and two =O groups]

(wherein $R^3$, $R^4$ and $R^5$ may be the same or different from each other and are each a hydrogen atom, a lower alkyl group or a lower alkoxy group) or a group represented by the formula:

[benzene ring structure with $R^3$, $R^4$, $R^5$, X, Y substituents]

(wherein $R^3$, $R^4$ and $R^5$ may be the same or different from each other and are each a hydrogen atom, a lower alkyl group or a lower alkoxy group, X and Y may be the same or different from each other and are each a hydroxyl group, a group represented by the formula $-(OCH_2)_n-OR^6$ (wherein n is 0 or 1 and $R^6$ is a lower alkyl group), or an acyl group), $R^1$ is an alkyl group having 2 to 20 carbon atoms, a cycloalkyl group, a cycloalkylalkyl group, an alkenyl group, an alkynyl group, an arylalkyl group, a group represented by the formula $-(CH_2)_p-CN$ (wherein p is an integer of 1 to 10), an alkyl substituted heteroaryl group a group represented by the formula $-(CH_2)_q-A$ (wherein q is an integer of 1 to 6), a group represented by the formula:

$$-\underset{\|}{\overset{(O)_r}{S}}-R^7$$

(wherein r is 0 or an integer of 1 to 2, $R^7$ is a lower alkyl group and cycloalkyl group or an aryl-group), or a group represented by the formula $-O-R^{11}$ (wherein $R^{11}$ is a lower alkyl group or an aryl group), or a group represented by the formula $-(CH_2-CH_2-O)_s-CH_3$ (wherein s is an integer of 1 to 3), $R^2$ is a group represented by the formula $-OR^8$ (wherein $R^8$ is a hydrogen atom or a lower alkyl group) or a group represented by the formula:

$$-N\overset{R^9}{\underset{R^{10}}{\diagup}}$$

(wherein $R^9$ and $R^{10}$ may be the same or different from each other and are each a hydrogen atom, a lower alkyl group, a hydroxyalkyl group or a heteroaryl group, provided that $R^9$ and $R^{10}$ may combine with each other to form a ring with a nitrogen atom bonded thereto, which further contain a nitrogen atom and/or an oxygen atom and may be substituted).

The term "lower alkyl group" used in the above-described definition of $R^3$, $R^4$, $R^5$, $R^6$, $R^7$ and $R^8$ for the compound of the present invention is intended to mean a straight-chain or branched alkyl group having 1 to 8 carbon atoms, and examples thereof include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 3-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and octyl groups. Among them, methyl, ethyl, propyl, isopropyl groups, etc., are preferable.

The term "lower alkoxy group" used in the definition of $R^3$, $R^4$ and $R^5$ is intended to mean a lower alkoxy group derived from the above-described lower alkyl group, such as methoxy, ethoxy and n-propoxy groups. Among them, a methoxy group is most desirable.

Preferred examples of a combination of $R^3$, $R^4$ and $R^5$ include one wherein $R^5$ is a methyl group and $R^3$ and $R^4$ are each a methoxy group, one wherein $R^3$, $R^4$ and $R^5$ are each a methoxy group, and one wherein $R^3$ is a methoxy group, $R^4$ is an ethoxy group and $R^5$ is a methyl group.

The term "alkyl group" in the definition of $R^1$ is intended to mean an alkyl group having 2 to 20 carbon atoms, with an alkyl group having 2 to 12 carbon atoms being preferred. An alkyl group having 7 to 12 carbon atoms is most desirable.

The term "cycloalkyl group" is intended to mean, e.g., a cycloalkyl group having 3 to 6 carbon atoms.

Preferred examples of the cycloalkylalkyl group include a cycloalkylmethyl group derived from the above-described cycloalkyl group having 3 to 6 carbon atoms.

The term "alkenyl group" is intended to mean a group having one or more double bonds in any portion of an alkyl group, and preferred examples thereof include the following groups:

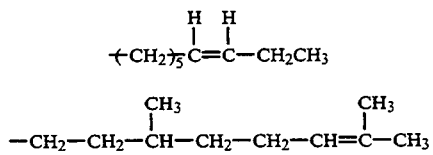

The term "alkynyl group" is intended to mean a group having one or more triple bonds in any portion of an alkyl group, and examples thereof include the following group:

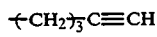

Representative examples of the arylalkyl group include a benzyl group wherein the phenyl ring may be substituted by one or more lower alkyl groups such as methyl and ethyl groups, lower alkoxy groups such as a methoxy group, a hydroxyl group, a carboxyl group or a halogen.

Representative examples of the alkyl substituted heteroaryl group include methyl substituted heteroaryl group wherein the heterocyclic ring may be substituted by a lower alkyl group such as a methyl group, a lower alkoxy group such as a methoxy group, a hydroxyl group or a halogen. Examples of the heteroaryl group include those containing a nitrogen, oxygen or sulfur atom, such as thiazolyl, pyranyl, thiadiazolyl and pyridyl groups.

In the group represented by the formula $-(CH_2)_p-CN$, wherein p is an integer of 1 to 10, p is most desirably an integer of 1 to 4.

In the group represented by the formula $-(CH_2)_q-B$, wherein q and B are as defined above, q is most desirably an integer of 1 to 4. In the definition of B, preferred examples of $R^7$ include methyl, cyclohexyl and phenyl groups.

When X and Y are each a hydroxyl group, the compound of the present invention is a hydroquinone compound.

In the definition of X and Y, $R^6$ is most desirably a methyl group and the acyl group may be derived from aliphatic, aromatic and heterocyclic compounds, and preferred examples of the acyl group include lower alkanoyl groups such as formyl, acetyl, propionyl, butyryl, valeryl, isovaleryl and pivaloyl, aroyl groups such as benzoyl, toluoyl and naphthoyl groups, and heteroaroyl groups such as furoyl, nicotinoyl and isonicotinoyl groups. Examples of preferred acyl groups include those derived from lower alkyl groups having 1 to 6 carbon atoms, i.e., acetyl, propionyl and butanoyl groups.

Examples of the pharmacologically acceptable salts include salts of benzoquinone derivatives with inorganic acids, such as hydrochloride, hydrobromide, sulfate, and phosphate; those with organic acids, such as acetate, maleate, tartrate, methanesulfonate, benzenesulfonate, and toluenesulfonate; and those with amino acid, such as arginine, aspartic acid, and glutamic acid.

Further, certain compounds of the present invention are in the form of metallic salts such as Na, K, Ca, or Mg salts, and these metallic salts as well are within the scope of the pharmacologically acceptable salts of the present invention.

Furthermore, as is apparent from, for example, the chemical structure, the compounds of the present invention each have a double bond, so they may be present in the form of stereoisomers (cis and trans isomers). As a matter of course, these also are within the scope of the present invention.

Representative processes for preparing the compound of the present invention will now be described.

Preparation process 1

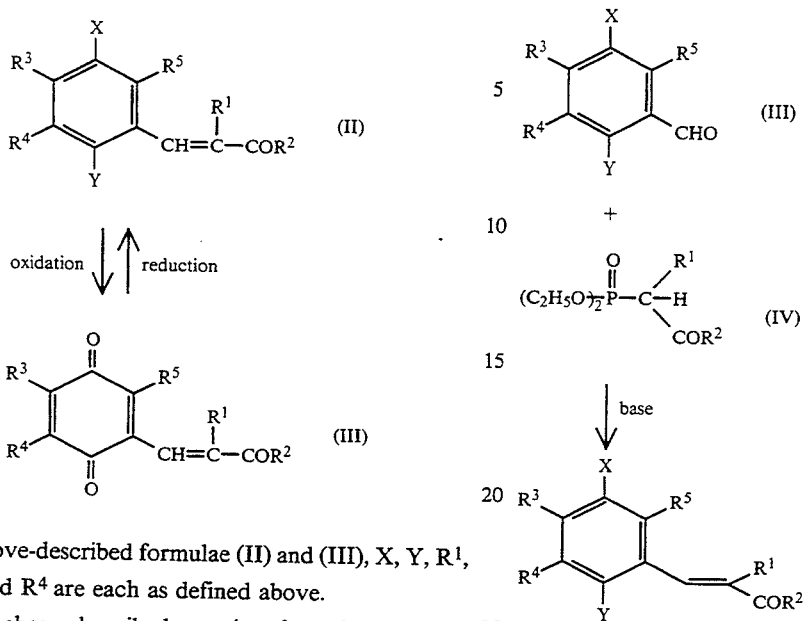

In the above-described formulae (II) and (III), X, Y, $R^1$, $R^2$, $R^3$ and $R^4$ are each as defined above.

In the above-described reaction formula, both the compounds (II) and (III) are the compounds of the present invention. As is apparent from the above-described reaction formula, a benzoquinone derivative as the compound (III) can be prepared by treating a hydroquinone derivative as the compound (II) with an oxidizing agent, while the compound (II) can be prepared by reducing the compound (III).

In order to oxidize the hydroquinone derivative as the compound (II), ferric chloride hexahydrate or lead oxide is used as the oxidizing agent. In this case, the oxidizing agent is used in an amount of preferably 3 to 10 times per mole of the hydroquinone derivative, and preferred examples of the solvent include benzene, ethyl acetate, dioxane, ethanol and 1,2-dimethoxyethane, each optionally containing water. The reaction is conducted at a temperature of 0° to 80° C., preferably 20° to 40° C. The reaction time is usually about 1 to 12 hr.

On the other hand, in order to reduce a quinone compound into a hydroquinone compound, which is one of the intended compounds of the present invention, preferred examples of the reducing agent include sodium borohydride and sodium hydrosulfite. Ethanol, tetrahydrofuran, ethyl acetate and 1,2-dimethoxyethane, each optionally containing water, are preferably used as the solvent. The reaction temperature is preferably 0° to 40° C., still preferably 0° to 20° C.

Preparation process 2

The hydroquinone compound (II), i.e., one of the intended compounds of the present invention can be prepared also by the following process.

In the above-described formulae, $R^1$, $R^2$, $R^3$, $R^4$, $R^5$, X and Y are each as defined above.

Specifically, an aldehyde derivative represented by the general formula (III) is subjected to the Wittig reaction (see, e.g., J.A.C.S., 83, 1733 (1961)) with a phosphonate represented by the general formula (IV) in the presence of a base to prepare an intended substance (II) represented by the general formula (II).

Examples of the base used in this reaction include alkali metal hydrides such as sodium hydride and potassium hydride and alkali metal alcoholates such as sodium methylate, sodium ethylate and tert-butoxypotassium. Preferred examples of the reaction solvent include benzene, toluene, dichloromethane, tetrahydrofuran, dioxane, dimethoxyethane and dimethylformamide. The reaction temperature is preferably 0° to 100° C., more preferably 20° to 80° C.

Preparation process 3

In the hydroquinone compound represented by the general formula (II), when X and $R^2$ are each a hydroxyl group, the compound of the present invention can be prepared also by the following process:

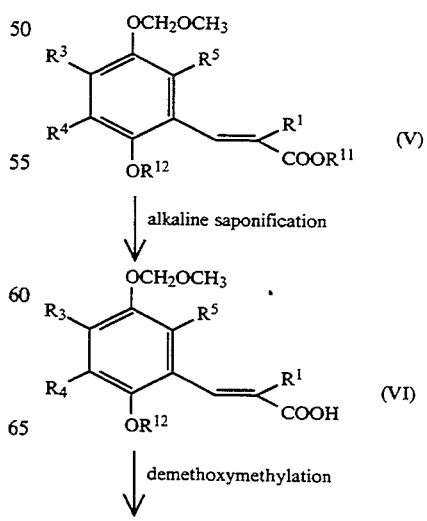

-continued

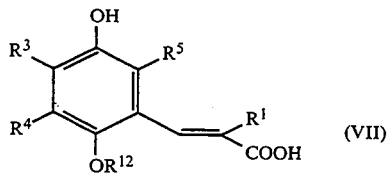 (VII)

In the above-described formulae, $R^1$, $R^3$, $R^4$, $R^5$ and Y are each as defined above and $R^{11}$ and $R^{12}$ are each a lower alkyl group.

Specifically, a compound represented by the general formula (V) is saponified with an alkali by a conventional method, and a compound represented by the general formula (VI) is demethoxymethylated to prepare a compound represented by the general formula (VII).

The saponification is conducted by making use of, e.g., an alcoholic caustic soda or caustic potash commonly used in the art. The demethoxymethylation is conducted in, e.g., acetone, dioxane, dimethoxyethane or an aqueous solution thereof in the presence of, e.g., mineral acids such as hydrochloric or sulfuric acid, or organic acids such as p-toluenesulfonic or camphorsulfonic acid. The reaction temperature is preferably 20° to 80° C.

The compound (VII) prepared by this process can be oxidized, e.g., by the same method as that described above in connection with the Preparation process 1 to easily prepare a compound represented by the general formula (VIII) which is one of the intended compounds of the present invention.

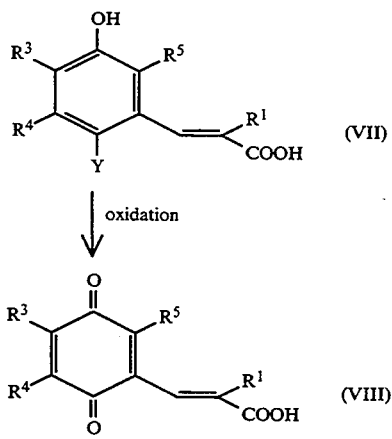

In the above-described formulae, $R^1$, $R^3$, $R^4$ and Y are each as defined above.

The above-described compound (VIII) as one of the intended compounds can be prepared also by oxidizing the above-described compound represented by the general formula (V).

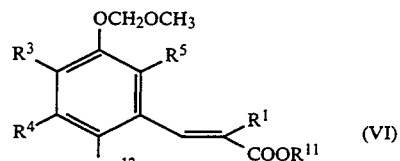 (VI)

↓ oxidation

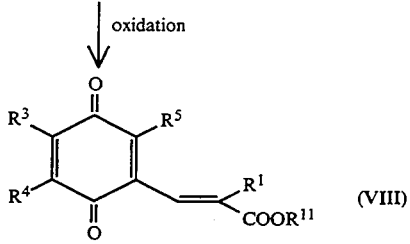 (VIII)

In the above-described formulae, $R^1$, $R^3$, $R^4$, Y, $R^{11}$ and $R^{12}$ are each as defined above.

In the oxidation, when direct oxidation is conducted by making use of an oxidizing agent such as ferric chloride hexahydrate, demethoxymethylation and oxidation simultaneously proceed, thereby enabling a quinone compound represented by the general formula (VIII) as one of the intended substances of the present invention to be prepared in one step.

Preparation process 4

In the general formula (I), when $R^2$ is a group represented by the formula:

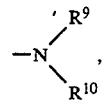

wherein $R^9$ and $R^{10}$ are each as defined above, the compound of the present invention can be prepared also by the following process:

$$A-CH=\overset{R^1}{\underset{}{C}}-COOH \quad (IX)$$

amidation ↓ $HN\overset{R^9}{\underset{R^{10}}{\diagdown}}$ (X)

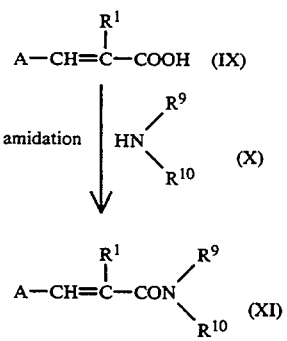 (XI)

In the above-described formulae, A, $R^1$, $R^9$ and $R^{10}$ are each as defined above.

Specifically, a carboxylic acid or its reactive derivative represented by the general formula (IX) can be reacted with an amino compound represented by the general formula (X) for amidation, thereby preparing a compound (XI) as one of the intended compounds.

Examples of reactive derivatives of the compound (IX) include acid halides such as acid chloride and acid bromide; acid azides; active esters with N-hydroxybenzotriazole, N-hydroxysuccinimide, etc.; symmetric acid anhydrides; and mixed acid anhydrides with alkylcarbonic acid, p-toluenesulfonic acid or the like.

When a free carboxylic acid is used as the compound (IX), the reaction is preferably conducted in the presence of a condensing agent such as dicyclohexylcarbodiimide, 1,1'-carbonyldiimidazole or the like.

The reaction is conducted by making use of the compound (IX) or its reactive derivative and the compound (X) in such a proportion that they are equimolar or the number of moles of one of them is slightly larger than that of the other, in an inert organic solvent, e.g., pyridine, tetrahydrofuran, dioxane, ether, benzene, toluene, xylene, methylene chloride, dichloroethane, chloroform, dimethylformamide, ethyl acetate or acetonitrile.

In the reaction, the addition of a base such as triethylamine, pyridine, picoline, lutidine, N,N-dimethylaniline, potassium carbonate or sodium hydroxide is often advantageous for smooth progress of the reaction depending upon the kind of the reactive derivative.

The reaction temperature varies depending upon the kind of the reactive derivative and is not particularly limited.

The hydroquinone derivative and the quinone derivative prepared by the Preparation process 4 can be oxidized and reduced by the Preparation process 1 described above to respectively prepare the quinone derivative and the hydroquinone derivative.

Specific examples of the case where the intended substance is a hydroquinone compound, X is a hydroxyl group and Y is a group represented by the formula —OR$^{12}$ wherein R$^{12}$ is a lower alkyl group will now be described.

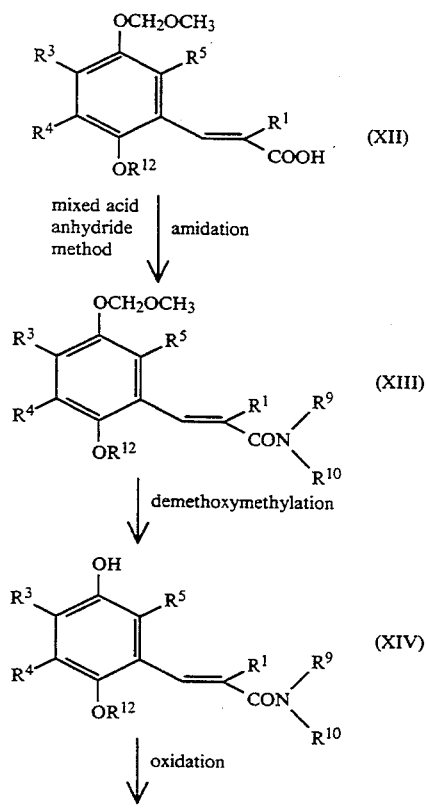

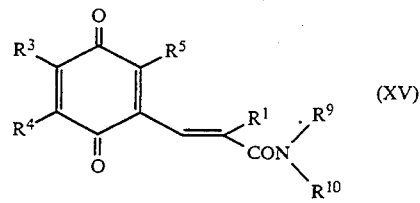

Process for preparing starting material (1) In the Preparation process 2, the compound represented by the general formula (IV) used as the starting material can be prepared, e.g., by the following process:

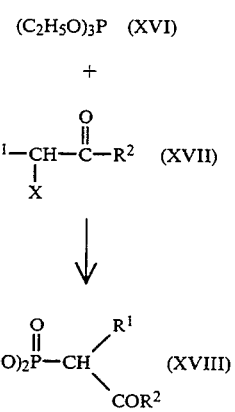

In the above-described formulae, R$^1$ and R$^2$ are each as defined above and X is a halogen atom.

Specifically, the starting material can be prepared by reacting triethylphosphite with an α-halogenated carboxylic acid derivative (XVII).

When R$^2$ is a group represented by the formula —OR$^8$, wherein R$^8$ is as defined above, the starting material can be prepared also by the following process:

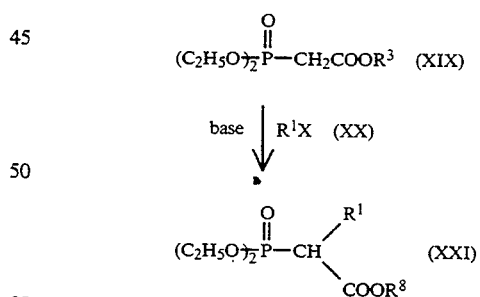

In the above-described formula, R$^1$ and R$^8$ are each as defined above and X is a halogen atom.

Specifically, the starting material can be easily synthesized by alkylating a triethylphosphonoacetic ester (XIX) with an alkyl halide in the presence of a base (see J. Org. Chem., 30, 2208 (1965)).

In this case, an alkali metal hydride such as sodium hydride or potassium hydride or an alkali metal alcoholate such as sodium methoxide, sodium ethoxide or tert-butoxypotassium is used as the base. Preferred examples of the solvent include dimethylformamide, dimethylacetamide, N-methylpyrrolidone, tetrahydrofuran and 1,2-dimethoxyethane. The reaction temperature is 20° to 80° C., preferably 40° to 60° C.

(2) In Preparation process 2, the starting material (III) used can be prepared, e.g., by the following process:

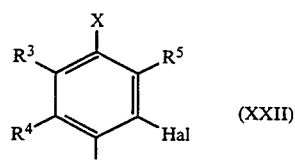

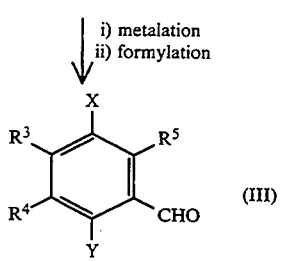

Specifically, the starting material can be prepared according to a conventional method by a halide represented by the general formula (XXII), wherein Hal is chlorine, bromide, iodine or the like, with an anion derived from an alkyl metal and a formylating agent. Examples of the alkyl metal include butyllithium, sec-butyllithium and LDA, while those of the formylating agent include dimethylformamide and N-methylformanilide. Examples of the solvent used in this reaction include ether, tetrahydrofuran and dimethoxyethane. The reaction temperature is about −80° to 0° C., preferably −60° to −30° C.

In the compound (XXII) used as the starting substance in the above-described process, a compound, wherein $R^3$ and $R^4$ are each a lower alkoxy group and $R^5$ is a methyl group, X is a methoxymethyloxy group and Y is an alkoxy group can be prepared, e.g., by the following process:

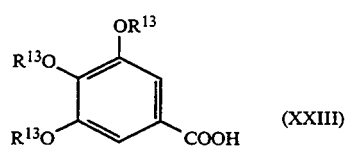

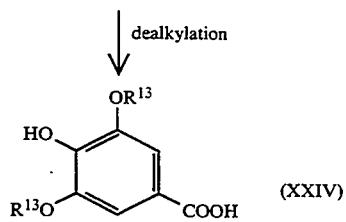

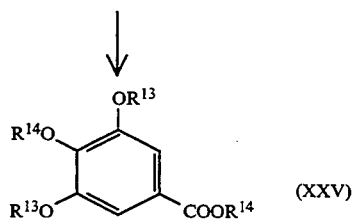

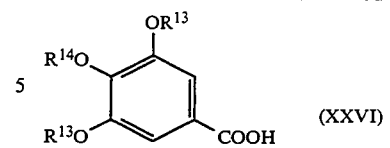

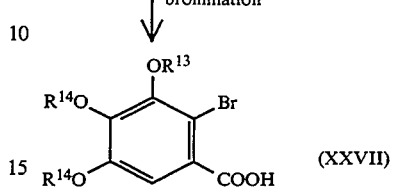

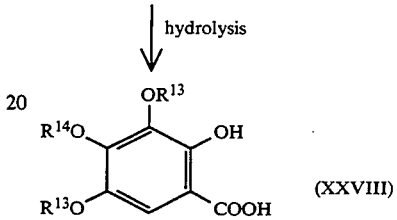

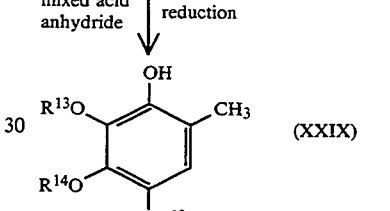

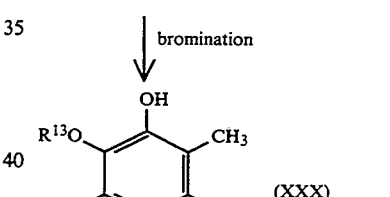

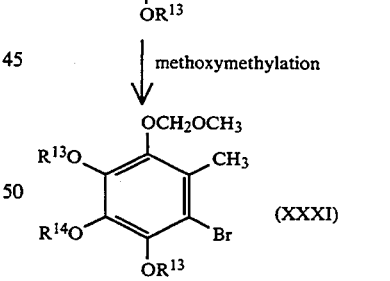

In the above-described formulae, $R^{13}$ and $R^{14}$ are each a lower alkyl group.

Specifically, a trialkyl ether of gallic acid (XXIII) can be heated in an acetic acid-concentrated hydrobromic acid solvent mixture to selectively cleave the ether bond at the 4-position, thereby preparing a compound represented by the general formula (XXIV).

Then, a suitable alkyl halide is reacted with this compound in the presence of a base to simultaneously conduct etherification and esterification, thereby preparing a compound represented by the general formula (XXV). An alkali metal hydride such as sodium hydride or potassium hydride and an alkali metal carbonate such as sodium carbonate or potassium carbonate may be used as the base.

The solvent is preferably dimethylformamide, dimethylacetamide, tetrahydrofuran, dioxane or the like, and the reaction temperature is 30° to 80°. The above compound is saponified with an alkali and then brominated by a conventional method to prepare a bromo compound (XXVII). This compound can be converted into a phenol compound (XXVIII) by heating the compound under reflux in the presence of a catalytic amount of a metallic copper in an aqueous concentrated alkali solution according to the method proposed by Meyer et al. (see Chem. Ber., 89, 511 (1956)).

A compound represented by the general formula (XXIX) can be prepared according to the method of Minami et al. (see Chem. Pharm. Bull., 28 (5), 1648 (1980)), i.e., by reacting the compound (XXVIII) with an ester of halogeno-carbonic acid, such as ethyl chlorocarbonate or isobutyl chlorocarbonate in the presence of a base to prepare a mixed acid anhydride and reducing the mixed acid anhydride with sodium borohydride or lithium borohydride to prepare a compound represented by the general formula (XXIX). Examples of the base used include organic bases such as triethylamine, pyridine and diisopropylethylamine and inorganic bases such as sodium carbonate and potassium carbonate. Tetrahydrofuran, ether, dioxane, dimethoxyethane or the like is used as a solvent, and the reaction temperature is preferably 0° to 30° C.

The compound (XXIX) may be brominated and methoxymethylated by a conventional method to convert it into an intended compound (XXXI). The bromination is conducted in a solvent such as chloroform, benzene, methanol or ethyl acetate at a reaction temperature of 0° to 30° C. The methoxymethylation is conducted by reacting the compound (XXX) with chloromethyl methyl ether in a solvent, such as dimethylformamide, dimethylacetamide, N-methylpyrrolidone, tetrahydrofuran, dimethoxyethane, dichloromethane or toluene, in the presence of an alkali metal hydride, such as sodium hydride or potassium hydride, and an organic base such as diisopropylethylamine or dimethylaminopyridine.

The bromo compound (XXXI) prepared above can be formylated by the following conventional method to prepare a formyl compound (XXXII):

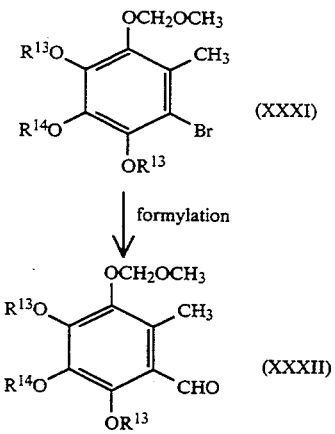

In the above-described formula, $R^{13}$ and $R^{14}$ are each a lower alkyl group.

In the Preparation process 2, when $R^3$, $R^4$ and $R^5$ in the compound represented by the general formula (III) are each a lower alkoxy group, X is a lower alkoxy group and Y is a methoxymethyloxy group, the compound can be prepared also by the following process:

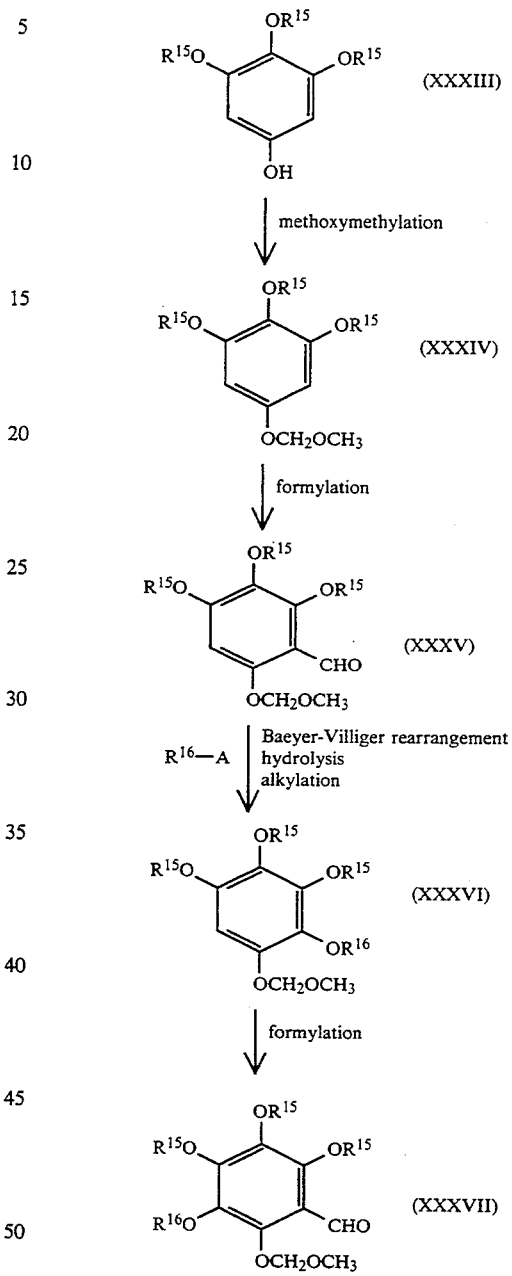

In the above-described formulae, $R^{15}$ and $R^{16}$ are each a lower alkyl group.

Specifically, 3,4,5-trialkoxyphenol (XXXIII) is methoxymethylated in the same manner as that described above, and the product is treated with an alkyl metal to form an anion, which is then reacted with a formylating agent to prepare a formyl compound (XXXV). In this case, an ether, tetrahydrofuran or the like, is used as the reaction solvent, and the reaction temperature is preferably 0° to 30° C. The formyl compound (XXXV) is subjected to a Baeyer-Villiger reaction with a peracid to prepare an O-formyl compound. The O-formyl compound is hydrolyzed to prepare a phenol compound, which is alkylated as such to prepare a compound represented by general formula (XXXVI). Examples of the peracid used in the Baeyer-Villiger reaction include peracetic acid, perbenzoic acid and m-chloroperbenzoic acid. Dichloromethane, chloroform, dichloroethane, etc., are preferred as the reaction solvent, and the reaction temperature is preferably 0° to 20° C. The compound (XXXVI) can be easily converted into a formylated compound (XXXVII) by reformylating the compound according to the above-described process.

The effect of the present invention will now be described in more detail by way of the following examples of pharmacological experiment on representative compounds of the present invention.

Pharmacological Tests

Test 1 effects on the rat D-galactosamine (GalN)-induced acute hepatitis model (1) Procedures 300 mg/kg of GalN was subcutaneously injected into a Fischer (F 344) male rat(s) (around 180 g) to induce acute hepatitis. Each test compound was suspended in a 0.5% aqueous methylcellulose solution and orally administered at a dose of 100 mg/kg one hr after the injection of GalN.

Blood was sampled from the tail of the rat 48 hr after the injection of GalN. The blood clotting time was measured by Hepaplastin test (HPT), and at the same time GPT activity in the plasma was measured enzymatically.

The percent inhibition of the GalN-induced hepatitis by each test compound is shown in Table 1.

(2) Results

Results are shown in Table 1. Refer to the Compounds in Tables 4 and 5.

TABLE 1

| Test compound | Percentage inhibition (%) | |
|---|---|---|
| | HPT | GPT |
| (compound No. 20) | 68 | 68 |
| (compound No. 79) | 89 | 94 |
| (compound No. 125) | 78 | 67 |

TABLE 1-continued

| Test compound | Percentage inhibition (%) | |
|---|---|---|
| | HPT | GPT |
| (compound No. 127) | 71 | 60 |
| (example No. 14) | 76 | 78 |
| (compound No. 135) | 51 | 52 |
| (compound No. 137) | 73 | 77 |
| (compound No. 141) | 98 | 100 |
| (compound No. 142) | 67 | 76 |
| (compound No. 144) | 79 | 78 |

TABLE 1-continued

| Test compound | Percentage inhibition (%) | |
|---|---|---|
| | HPT | GPT |
| (compound No. 149) [structure: MeO, MeO, OMe, O, O, cyclohexyl, COOH] | 95 | 93 |
| (example No. 4) [structure: MeO, MeO, Me, O, O, C₉H₁₉, COOH] | 87 | 91 |
| (compound No. 176) [structure: MeO, MeO, Me, O, O, CN, COOH] | 97 | 96 |
| (compound No. 183) [structure: MeO, MeO, Me, O, O, SMe, COOH] | 80 | 86 |
| (compound No. 217) [structure: MeO, MeO, Me, O, O, thiophene, COOH] | 99 | 97 |

Test 2 concerning effects on the mouse propionibactrium acnes (P. acnes)-lipopolysaccharide (LPS)-induced fulminant hepatitis model (1) Procedures One rag/mouse of heat-killed P. acnes was intravenously injected into a five-week-old male Balb/c mice and LPS was additionally intravenously injected at a dose of 1 microgram/mouse 7 days after the injection of P. acnes to induce fulminant hepatitis. Each test compound was suspended in a 0.5% methylcellulose solution and orally administered at a dose of 100 mg/kg 30 min before the intravenous injection of LPS.

Survival rates and GPT activity in plasma of the survivors were determined in 24 hours after the intravenous injection of LPS. The mice treated with each test compound against the lethality and hepatic injury induced with P. acnes-LPS are shown in Table 2.

(2) Results

The results are given in Table 2.

As with Table 1, the compound Nos. in Table 2 correspond to those of Tables 4 and 5.

TABLE 2 (part 1)

Effect of test compounds on P. acnes-LPS-induced death and hepatopathy

| Test compd. | Survival rate (%) control group (%) / test compd. group (%) | GPT (survival rate) control group (%) / test compd. group (%) |
|---|---|---|
| compd. No. 20 | 30/70 | 848 ± 316/293 ± 65 |
| compd. No. 79 | 8/50 | 1639/1009 ± 196 |
| compd. No. 125 | 40/90 | 353 ± 67/219 ± 52 |
| compd. of Ex. No. 14 | 40/100 | 485 ± 139/297 ± 50 |
| compd. No. 135 | 0/50 | — |
| compd. No. 137 | 0/30 | — |
| compd. No. 141 | 0/25 | — |
| compd. No. 142 | 22/100 | 761/381 ± 19 |
| compd. No. 144 | 36/100 | 696 ± 160/280 ± 31 |
| compd. No. 149 | 40/67 | 353 ± 67/209 ± 66 |
| compd. of Ex. No. 4 | 22/64 | 761/358 ± 40 |
| compd. No. 176 | 22/80 | 761/297 ± 50 |
| compd. No. 183 | 0/22 | — |
| compd. No. 217 | 0/80 | — |

Experimental Example 3

Toxicity test

The compound of the present invention prepared in Example 4, compound No. 137 prepared in Example 15 and compound No. 142 prepared in Example 15, as will be described hereinbelow, were orally administered to a seven-week male slc: SD rat for one week (dose: 300 mg/μg). As a result, no compound was found to cause death.

As is apparent from Experimental Examples 1 and 2, the compounds of the present invention are highly useful as a therapeutic agent for hepatic diseases.

Therefore, the compounds of the present invention are useful as a therapeutic and preventive agent for various types of hepatopathy of animals including human beings and can be specifically used for the treatment and prevention of, e.g., chronic hepatitis, acute hepatitis, toxic hepatopathy, viral hepatitis, alcoholic hepatitis, jaundice, and cirrhosis as an end-stage disease.

Further, as is apparent from Experimental Example 3, the compounds of the present invention have a very low toxicity, i.e., are highly safe. In many cases, the compounds of the present invention must be repetitively administered for a long period of time depending on the nature of the disease. In this respect as well, the present invention is of great value.

When the compounds of the present invention are used as a therapeutic and preventive agent for hepatic diseases, they may be orally administered in the form of powders, granules, capsules, syrups, etc., or parenterally administered in the form of suppositories, injections, external preparations and drops. The dose of the compounds of the present invention will remarkably vary depending upon the symptom, age, and kind of the hepatic disease, etc. In general, the compounds of the present invention may be administered in a dose of about 0.1 to 1,000 mg, preferably 2 to 500 mg., still preferably 5 to 150 mg per adult per day in one to several portions.

Pharmaceutical preparations are prepared from the compounds of the present invention by making use of a commonly accepted carrier for pharmaceutical preparations according to conventional methods.

Specifically, when a solid preparation for oral administration is prepared, the active ingredient is blended with a vehicle and, if necessary, a binder, a disintegrator, a lubricant, a colorant, a corrigent, etc., followed by preparation of tablets, coated tablets, granules, powders and capsules.

Examples of the vehicle include lactose, corn starch, sucrose, glucose, sorbitol, crystalline cellulose and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricant include magnesium stearate, talc, polyethylene glycol, silica and hydrogenated vegetable oil. Any colorant of which the addition to pharmaceuticals is officially allowed can be used as the colorant. Examples of the corrigent include cacao powder, menthol, aromatic powder, mentha powder, borneol and powdered cinnamon bark. It is a matter of course that a sugar coating, a gelatin coating and, if necessary, suitable other coatings may be applied on these tablets and granules.

When injections are prepared, a pH modifier, a buffering agent, a stabilizer, a solubilizing agent, etc., are added to the active ingredient, followed by the preparation of subcutaneous, intramuscular and intravenous injections according to conventional methods.

Representative Examples of the present invention will now be described, though it is needless to say that the present invention is not limited to them.

Since the compounds of the present invention have a double bond, they are expected to be present in the form of cis and trans isomers. In the following Examples, the compounds of the present invention are in the form of a trans isomer unless otherwise specified.

The final step of preparing the intended substance of the present invention will be described as Examples, and the steps of preparing the starting substance used in the Examples will be described as Referential Examples prior to the Examples.

The following symbols in the chemical structural formulae have the following meanings:
Me: methyl group
Et: ethyl group
n-Pr: n-propyl group
MOMO: methoxymethyloxy group
iso-Pr: isopropyl group
Oct: octyl group Referential Example 1

3,5-Diethoxy-4-hydroxybenzoic acid

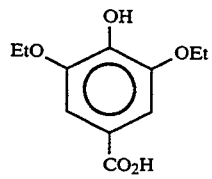

100 g of 3,4,5-triethoxybenzoic acid was dissolved in 150 ml of a 48% aqueous HBr solution and 300 ml of acetic acid, and the resultant solution was heated at 100° C. for 2 hr while stirring. The reaction mixture was cooled, and the formed precipitate was separated by filtration and washed with water. The solid was recrystallized from 1 l of ethanol to prepare 50 g of the product compound as a white solid.

Referential Example 2

Methyl 3,5-diethoxy-4-methoxybenzoate

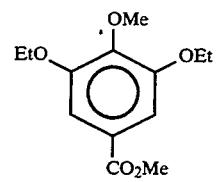

50 g of 3,5-diethoxy-4-hydroxybenzoic acid prepared in the Referential Example 1 was dissolved in 300 ml of DMF, and 153 g of potassium carbonate was added thereto. 41.3 ml of iodomethane at room temperature was added thereto, and the mixture was heated at 50° C. for 6 hr while stirring. The reaction mixture was cooled and poured into ice water and extracted with ethyl acetate. The extract was washed with water and dried over anhydrous magnesium sulfate, and the solvent was distilled off to prepare 63 g of the crude product-(white solid).

$^1$H-NMR (CDCl$_3$) δ; 1.45 (t, J=7 Hz, 6H), 3.87 (s, 3H), 3.88 (s, 3H), 4.12 (q, J=7 Hz, 4H), 7.22 ( s, 2H)

Referential Example 3

3,5-Diethoxy-4-methoxybenzoic acid

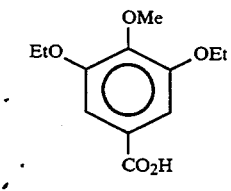

63 g of methyl 3,5-diethoxy-4-methoxybenzoate prepared in Referential Example 2 was dissolved in 200 ml of ethanol and 80 ml of water and 44 g of caustic soda was added thereto. The mixture was heated at 70° C. for 2 hr while stirring, cooled, weakly acidified with dilute hydrochloric acid and extracted with dichloromethane. The organic phase was washed with water and dried over anhydrous magnesium sulfate, and the solvent was then distilled off to prepare 48 g of the crude product (white solid).

$^1$H-NMR (CDCl$_3$) δ; 1.48 (t, J=7 Hz, 6H), 3.95 (s, 3H), 4.15 (q, J=7 Hz, 4H), 7.36 (s, 2H)

Referential Example 4

2-Bromo-3,5-diethoxy-4-methoxybenzoic acid

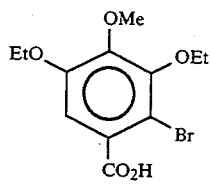

48 g of 3,5-diethoxy-3-methoxybenzoic acid prepared in Referential Example 3 was dissolved in 300 ml of chloroform, and 6 ml of water was added thereto. Then, 13.4 ml of bromine was dropwise added thereto over a period of 8 hr under reflux in chloroform. The solvent was concentrated in vacuo to prepare 68 g of the crude product (light yellow solid).

$^1$H-NMR (CDCl$_3$) δ; 1.46 (t, J=7 Hz, 3H), 1.47 (t, J=7 Hz, 3H), 3.95 (s, 3H), 4.08 (q, J=7 Hz, 4H), 7.34 (s, 1H)

Referential Example 5

3,5-Diethoxy-2-hydroxy-4-methoxybenzoic acid

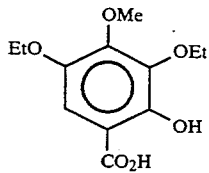

68 g of 2-bromo-3,5-diethoxy-4-methoxybenzoic acid prepared in Referential Example 4 was suspended in 260 ml of water and 32 g of caustic soda and 0.88 g of copper powder were added thereto. The mixture was heated at 120° C. for 3 hr while stirring, and then cooled. Carbon was added thereto, and the mixture was filtered through Celite. The filtrate was neutralized with 140 ml of 6N hydrochloric acid and 1 l of chloroform was added thereto. The mixture was subjected to liquid-liquid separation. The organic phase was washed with water, dried and then concentrated to prepare 53 g of the crude product (ocherous solid).

$^1$H-NMR (CDCl$_3$) δ; 1.40 (t, J=7 Hz, 3H), 1.43 (t, J=7 Hz, 3H), 4.00 (s, 3H), 4.02 (q, J=7 Hz, 2H), 4.13 (q, J=7 Hz, 2H), 7.11 (s, 1H)

Referential Example 6

2,4-Diethoxy-3-methoxy-6-methylphenol

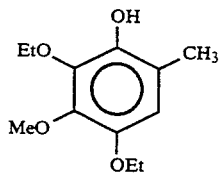

53 g of 3,5-diethoxy-2-hydroxy-3-methoxybenzoic acid prepared in Referential Example 5 and 45.5 g of triethyl amine were dissolved in 400 ml of THF, and 48.4 g of ethyl chlorocarbonate in 100 ml of THF was dropwise added thereto with ice cooling while stirring. After the completion of the dropwise addition, the formed crystals were separated by filtration and washed with 100 ml of THF. The mother liquor was combined with the wash liquid, and a 10% aqueous solution of 30.3 g of sodium borohydride was added to the resultant solution and cooled by ice while stirring. After the completion of the dropwise addition, the mixture was stirred at room temperature for one hr, neutralized with dilute hydrochloric acid and extracted with ethyl acetate. The organic phase was washed with water, dried over anhydrous magnesium sulfate and concentrated. The concentrate was purified by silica gel column chromatography (eluent: n-hexane:ethyl acetate=95.5) to prepare 40 g of the product compound as a colorless oleaginous substance.

$^1$H-NMR (CDCl$_3$) δ; 1.38 (t, J=7 Hz, 3H), 1.40 (t, J=7 Hz, 3H), 2.19 (s, 3H), 3.84 (s, 3H), 3.98 (q, J=7 Hz, 2H), 4.18 (q, J=7 Hz, 2H), 5.45 (s, 1H), 6.39 (s, 1H)

Referential Example 7

5-Bromo-2,4-diethoxy-3-methoxy-6-methylphenol

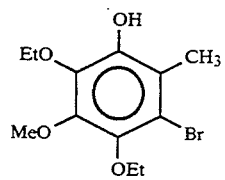

40 g of 2,4-diethoxy-3-methoxy-6-methylphenol prepared in Referential Example 6 was dissolved in 200 ml of chloroform, and 10 ml of bromine was added thereto and cooled by ice while stirring. Ice water was added to the reaction mixture, and the mixture was subjected to liquid-liquid separation. The organic phase was washed with saturated saline and dried over anhydrous magnesium sulfate, and the solvent was distilled off to prepare 54 g of the product compound as a light yellow oleaginous substance.

$^1$H-NMR (CDCl$_3$) δ; 1.38 (t, J=7 Hz, 3H), 1.40 (t, J=7 Hz, 3H), 2.28 (s, 3H), 3.87 (s, 3H), 3.97 (q, J=7 Hz, 2H), 4.16 (q, J=7 Hz, 2H), 5.71 (br, 1H)

Referential Example 8

5-Bromo-2,4-diethoxy-6-methyl-1-methoxymethyloxy-benzene

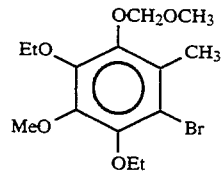

54 g of 5-bromo-2,4-diethoxy-3-methoxy-6-methylphenol prepared in Referential Example 7 was dissolved in 250 ml of DMF, and 8.5 g of sodium hydride (55% oil suspension) was added thereto and cooled by ice while stirring. The mixture was stirred at room temperature for 30 min and cooled again with ice, and 17.1 g of methoxymethyl chloride was dropwise added thereto. After the completion of the dropwise addition, the mixture was further stirred at room temperature for 30 min. Ice water was added thereto, and the mixture was extracted with ethyl acetate. The organic phase was washed with water, dried over anhydrous magnesium sulfate, concentrated and purified by silica gel column chromatography (eluent; n-hexane:ethyl acetate=95:5) to prepare 43.6 g of the product compound as a colorless oleaginous substance.

$^1$H-NMR (CDCl$_3$) δ; 1.37 (t, J=7 Hz, 3H), 1.41 (t, J=7 Hz, 3H), 2.36 (s, 3H), 3.58 (s, 3H), 3.88 (s, 3H), 4.02 (q, J=7 Hz, 2H), 4.03 (q, J=7 Hz, 2H), 5.04 (s, 2H)

Referential Example 9

2,4-Diethoxy-3-methoxy-5-methoxymethyloxy-6-methylbenzaldehyde (starting compound No. (8))

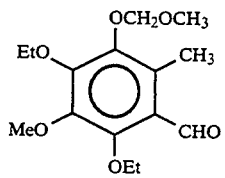

43.6 g of 5-bromo-2,4-diethoxy-6-methyl-1-methoxymethyloxybenzene prepared in Referential Example 8 was dissolved in 220 ml of THF, and 100 ml of n-butyllithium (1.6M n-hexane solution) was dropwise added thereto at −70° C. The mixture was stirred at −40° C. for 30 min, and 11.9 g of dimethylformamide was dropwise added thereto. The temperature of the reaction mixture was returned to room temperature, and an aqueous ammonium chloride solution was added thereto, followed by extracting with ethyl acetate. The organic phase was washed with-water, dried, concentrated and purified by silica gel column chromatography (eluent; n-hexane:ethyl acetate=90:10) to prepare 19.2 g of the product compound as a colorless oleaginous substance.

$^1$H-NMR; 1.40 (t, J=7 Hz, 6H), 2.49 (s, 3H), 3.58 (s, 3H), 3.88 (s, 3H), 4.10 (q, J=7 Hz, 2H), 4.18 (q, J=7 Hz, 2H), 5.01 (s, 2H), 10.37 (s, 1H)

Referential Example 10

1-Methoxymethyloxy-3,4,5-trimethoxyphenol

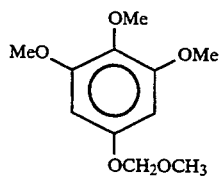

25 g of 3,4,5-trimethoxyphenol was dissolved in 100 ml of DMF, and 7.1 g of sodium hydride (55% oil suspension) was added thereto and cooled by ice while stirring. Then, 12.4 ml of methoxymethyl chloride was added thereto with ice cooling, and the mixture was stirred at room temperature for 30 min. The reaction mixture was poured into ice water and extracted with ethyl acetate. The organic phase was washed with water and dried over anhydrous magnesium sulfate, and the solvent was distilled off. The residue was purified by silica gel column chromatography (eluent; n-hexane:ethyl acetate=85:15) to prepare 30.4 g of the product compound as a colorless oleaginous substance.

Referential Example 11

2-Methoxymethyloxy-4,5,6-trimethoxybenzaldehyde (starting compound No. (9))

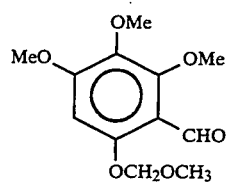

30.4 g of t-methoxymethyloxy-3,4,5-trimethoxyphenol prepared in Referential Example 10 was dissolved in 250 ml of anhydrous ether, and 100 ml of n-butyllithium (1.6M n-hexane solution) was dropwise added thereto at −20° C. After the completion of the dropwise addition, the mixture was stirred at room temperature for 2 hr, and 14.6 ml of DMF was added thereto. 100 ml of ice water was added thereto, and the mixture was extracted with ethyl acetate. The organic phase was washed with water and dried over anhydrous magnesium sulfate, and the solvent was distilled off. The residue was purified by silica gel column chromatography (eluent; n-hexane:ethyl acetate=6:4) to prepare 25.5 g of the product compound as a light yellow oleaginous substance.

$^1$H-NMR; 3.48 (s, 3H), 3.78 (s, 3H), 3.88 (s, 3H), 3.92 (s, 3H), 5.20 (s, 2H), 6.50 (s, 1H), 10.22 (s, 1H)

Referential Example 12

2-Methoxymethyloxy-4,5,6-trimethoxyphenol

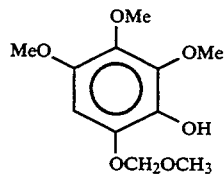

12.8 g of 2-methoxymethyloxy-4,5,6-trimethoxybenzaldehyde prepared in Referential Example 11 was dissolved in 100 ml of dichloromethane, and 8.7 g of m-chloroperbenzoic acid was added thereto at room temperature while stirring. The mixture was refluxed for 30 min and cooled with ice, and 100 ml of a saturated aqueous sodium thiosulfate solution was added thereto. The precipitated crystals were separated by filtration. The mother liquor was washed with a saturated aqueous sodium hydrogen-carbonate solution, dried over anhydrous magnesium sulfate and concentrated. The residue was mixed with 50 ml of ethanol, 40 ml of water and 21.3 g of potassium hydroxide, and the mixture was stirred for 1 hr under reflux. The reaction mixture was cooled, poured into dilute hydrochloric acid and extracted with ethyl acetate. The organic phase was washed with water and dried over anhydrous magnesium sulfate, and the solvent was distilled off to prepare 11.5 g of the product compound (light yellow oleaginous) as a crude product.

Referential Example 13

1-Methoxymethyloxy-2,3,4,5-tetramethoxybenzene

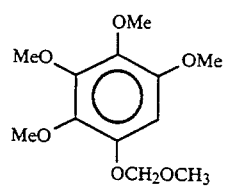

11.5 g of 2-methoxymethyloxy-4,5,6-trimethoxyphenol prepared in Referential Example 12 and 23.0 g of potassium carbonate were suspended in 100 ml of DMF. The suspension was heated at 45° C. while stirring, and 5.2 ml of iodomethane was dropwise added thereto. After the completion of the dropwise addition, the mixture was heated for 30 min, cooled and separated by filtration. 1 l of water was added to the mother liquor, and the mixture was extracted with ethyl acetate. The organic phase was washed with water and dried over anhydrous magnesium sulfate, and the solvent was distilled off. The residue was purified by silica gel column chromatography (eluent; n-hexane:ethyl acetate=85:15) to prepare 6.2 g of the product compound as a colorless oleaginous substance.

NMR (CDO$_3$) δ; 3.52 (s, 3H), 3.78 (s, 3H), 3.82 (s, 6H), 3.94 (s, 3H), 5.16 (s, 2H), 6.50 (s, 1H)

Referential Example 14

2-Methoxymethyloxy-3,4,5,6-tetramethoxybenzaldehyde (starting compound No. (10))

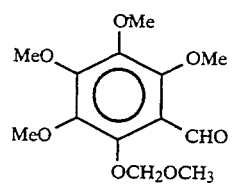

6.2 g of 1-methoxymethyloxy-2,3,4,5-tetramethoxybenzene prepared in Referential Example 13 was dissolved in 50 ml of anhydrous ether, and 18 ml of n-butyllithium (1.6M n-hexane solution) was dropwise added thereto at −20° C. while stirring. After the mixture was stirred at 0° C. for 30 min, the temperature was returned to −20° C. and 3.5 ml of DMF was dropwise added thereto. After 100 ml of water was added thereto, the mixture was extracted with ethyl acetate, and the organic phase was washed with water, dried over anhydrous magnesium sulfate and concentrated. The residue was purified by silica gel column chromatography (eluent; n-hexane:ethyl acetate=7:3) to prepare 5.6 g of the product compound as a light yellow oleaginous substance.

$^1$H-NMR (δ); 3.56 (s, 3H), 3.84 (s, 3H), 3.86 (s, 3H), 3.90 (s, 3H), 4.02 (s, 3H), 5.12 (s, 2H), 10.06 (s, 1H)

The following starting compounds (1) to (7) were prepared in the same manner as that of Reference Examples 2 to 9. The spectral data of the compounds are given in the following Table 3.

TABLE 3

| Starting compd. No. | Product | $^1$H-NMR |
|---|---|---|
| (1) | MeO, MeO, OCH$_2$OCH$_3$, CH$_3$, CHO, OMe<br>light yellow oil | 2.48(s, 3H), 3.58(s, 3H), 3.88(s, 3H), 3.92(s, 3H), 3.96(s, 3H), 5.00(s, 2H), 10.37(s, 1H) |
| (2) | EtO, EtO, OCH$_2$OCH$_3$, CH$_3$, CHO, OEt<br>light yellow oil | 1.40(t, J=7Hz, 9H), 2.48(s, 3H), 3.58(s, 3H), 4.06(q, J=7Hz, 2H), 4.12(q, J=7Hz, 2H), 4.18(q, J=7Hz, 2H), 5.02(s, 2H), 10.39(s, 1H) |
| (3) | MeO, EtO, OCH$_2$OCH$_3$, CH$_3$, CHO, OMe<br>light yellow oil | 1.40(t, J=7Hz, 3H), 2.49(s, 3H), 3.57(s, 3H), 3.93(s, 3H), 3.97(s, 3H), 4.09(q, J=7Hz, 2H), 5.00(s, 2H), 10.36(s, 1H) |

TABLE 3-continued

| Starting compd. No. | Product | ¹H-NMR |
|---|---|---|
| (4) | 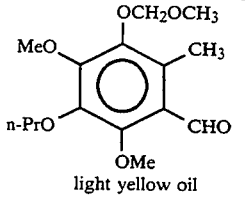light yellow oil | 1.06(t, J=7.0Hz, 3H), 1.60-1.97(m, 2H), 2.49(s, 3H), 3.57(s, 3H), 3.91(q, J=7.0Hz, 2H), 3.91(s, 3H), 3.96(s, 3H), 5.00(s, 2H), 10.39(s, 1H) |
| (5) | 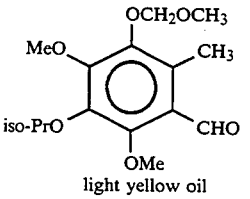light yellow oil | 1.29(d, J=6.4Hz, 6H), 2.49(s, 3H), 3.57(s, 3H), 3.90(s, 3H), 3.94(s, 3H), 4.34(hept, J=6.4Hz, 1H), 4.99(s, 2H), 10.34(s, 1H) |
| (6) | 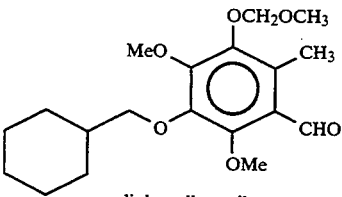light yellow oil | 0.77-2.09(m, 11H), 2.47(s, 3H), 3.57(s, 3H), 3.77(d, J=6.2Hz, 2H), 3.90(s, 3H), 3.93(s, 3H), 5.00(s, 2H), 10.51(s, 1H) |
| (7) | 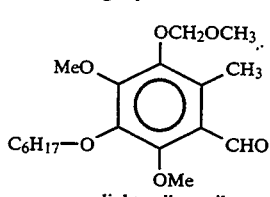light yellow oil | 0.88(t, J=6Hz, 3H), 1.61-1.59(m, 10H), 1.59-1.95(m, 2H), 2.48(s, 3H), 3.58(s, 3H), 3.90(s, 3H), 3.92(s, 3H), 3.98(t, J=7Hz, 2H), 5.00(s, 2H), 10.34(s, 1H) |

EXAMPLE 1

Ethyl(E)3-[5-(6-methyl-1-methoxymethyloxy-2,3,4-trimethoxy)phenyl]-2-nonyl-2-propenoate

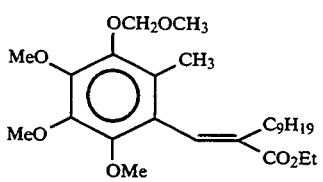

0.6 g of sodium hydride (60% oil suspension) was suspended in 5 ml of DMF, and 8.8 g of ethyl diethylphosphono-2-undecanoate was dropwise added to the suspension. After the reaction mixture became homogeneous, 2.7 g of 5-methoxymethyloxy-6-methyl2,3,4-trimethoxybenzaldehyde (compound No. (1)) prepared in the same manner as that of Referential Examples 1 to 9 was dropwise added thereto at room temperature. After the completion of the dropwise addition, the mixture was heated at 60° to 70° C. for one hr, poured into ice water and extracted with ethyl acetate. The organic phase was washed with water and dried over anhydrous magnesium sulfate, and the solvent was distilled off. The residue was purified by silica gel column chromatography (eluent; n-hexane:ethyl acetate=95:5) to prepare 3.9 g of the product compound.

¹N-NMR (δ): 0.86 (t, J=6 Hz, 3H), 1.00-1.50 (n, 14H), 1.36 (t, J=7 Hz, 3H), 2.08 (s, 3H), 2.00-2.25 (m, 2H), 3.58 (s, 3H), 3.68 (s, 3H), 3.88 (s, 6H), 4.24 (q, J=7 Hz, 2H), 5.04 (s, 2H), 7.33 (s, 1H)

Compounds Nos. 1 to 8 were prepared in the same manner as that of Example 1.

EXAMPLE 2

(E)-3-[5-(6-Methyl-1-methoxymethyloxy-2,3,4-trimethoxy)phenyl]-2-propenoic acid

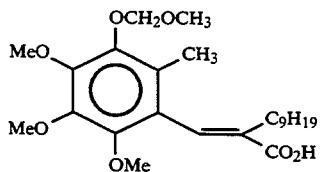

3.9 g of ethyl(E)-3-[5-(6-methyl-1-methoxymethyloxy-2,3,4-trimethoxy)phenyl]-2-nonyl-2-propenoate prepared in Example 1 was dissolved in 30 ml of ethanol and 5 ml of water, and 1.7 g of sodium hydroxide was added thereto. The mixture was stirred for 1 hr under reflux, cooled and extracted with n-hexane, and the aqueous phase was acidified with 1N dilute hydrochloric acid. Extraction was conducted with dichloromethane, and the organic phase was washed with water and dried over anhydrous magnesium sulfate. The solvent was distilled off to prepare 3.6 g of the product compound as a colorless oleaginous substance.

$^1$H-NMR (δ): 0.86 (t, J=6 Hz, 3H), 1.01–1.59 (m, 14H), 2.00–2.28 (m, 2H), 2.10 (s, 3H), 3.59 (s, 3H), 3.69 (s, 3H), 3.88 (s, 6H), 5.04 (s, 2H), 7.50 (s, 1H)

Compounds Nos. 9 to 16 were prepared in the same manner as that of Example 2.

EXAMPLE 3

(E)-3-[5-(1-Hydroxy-6-methyl-2,3,4-trimethoxy)-phenyl]-2-nonyl-2-propenoic acid

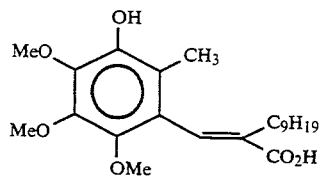

3.6 g of (E)3-[5-(6-methyl-1-methoxymethyloxy2,3,4-trimethoxy)phenyl]-2-nonyl-2-propenoic acid prepared in Example 2 was dissolved in 30 ml of acetone and 7 ml of 6N hydrochloric acid, and the resultant solution was heated at 70° C. for 1 hr while stirring. The reaction mixture was cooled and 100 of water added thereto. The mixture was extracted with dichloromethane, and the organic phase was washed with water, dried over anhydrous magnesium sulfate, and concentrated to prepare 3.4 g of the product compound as a colorless oleaginous substance.

$^1$H-NMR (δ): 0.86 (t, J=6 Hz, 3H), 1.01–1.60 (m, 14H), 2.01–2.32 (m, 2H), 2.07 (s, 3H), 3.68 (s, 3H), 3.89 (s, 3H), 3.97 (s, 3H), 7.57 (s, 1H)

Compounds Nos. 17 to 124 were prepared in the same manner as that of Example 3.

EXAMPLE 4

(E)-3-[5-(2,3-Dimethoxy-6-methyl-1,4-benzoquinoyl)]-2-nonyl-2-propenoic acid

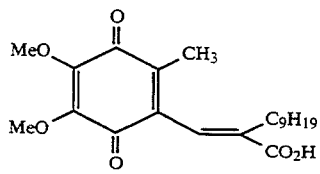

3.4 g of (E)3-[5-(1-hydroxy-6-methyl-2,3,4-trimethoxy)phenyl]-2-nonyl-2-propenoic acid prepared in Example 3 was dissolved in 100 ml of ethyl acetate and 3.4 g of ferric chloride hexahydrate was added thereto. The mixture was stirred at room temperature for 2 hr and 200 ml of water was added thereto. The resulting mixture was separated into two liquid phases and the organic phase was washed with water and dried over anhydrous magnesium sulfate. The solvent was distilled off, and the residue was purified by silica gel column chromatography (eluent; dichloromethane:methanol=95:5) and recrystallized from n-hexane to prepare 2.9 g of the product compound as an orange solid melting point: 68° C.

$^1$H-NMR (δ): 0.86 (t, J=6 Hz, 3H), 1.02–1.60 (m, 14H), 1.96 (d, J=2 Hz, 3H), 2.01–2.22 (m, 2H), 3.99 (s, 3H), 4.01 (s, 3H), 7.20 (bs, 1H)

Compounds Nos. 130 to 237 were prepared in the same manner as that of Example 4.

EXAMPLE 5

N-[(E)-3-[5-(6-Methyl-1-methoxymethyloxy-2,3,4-trimethoxy)phenyl]-2-nonyl-2-propenoyl]morpholine

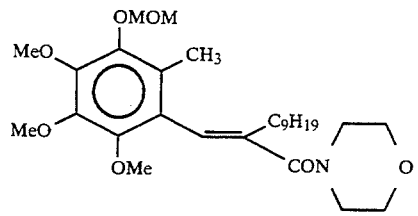

1.0 g of (E)-3-[5-(6-methyl-1-methoxymethyloxy-2,3,4-trimethoxy)phenyl]-2-nonyl-2-propenoic acid prepared in Example 2 and 1.0 ml of triethylamine were dissolved in 10 ml of tetrahydrofuran, and 0.45 ml of diethylphosphonic acid chloride was dropwise added thereto and cooled by ice while stirring. After the mixture was stirred at room temperature for 30 min, 1.0 ml of morpholine was added thereto, and the mixture was stirred as such for 2 hr. Water was added to the reaction mixture, and the mixture was extracted with ethyl acetate. The organic phase was washed with water and then dried over anhydrous magnesium sulfate. The solvent was distilled off, and the residue was purified by silica gel column chromatography (eluent; n-hexane:ethyl acetate=3:2) to prepare 0.93 g of the product compound as a colorless oleaginous substance.

$^1$H-NMR (δ): 0.86 (t, J=6 Hz, 3H), 1.00–1.50 (m, 14H), 2.12 (s, 3H), 2.00–2.20 (m, 2H), 3.50–3.80 (m, 8H), 3.56 (s, 3H), 3.68 (s, 3H), 3.88 (s, 6H), 5.04 (s, 2H), 6.12 (s, 1H)

EXAMPLE 6

N-[(E)-3-[5(2,3-Dimethoxy-6-methyl-1,4-benzoquinoyl)]-2-nonyl-2-propenoyl]morpholine

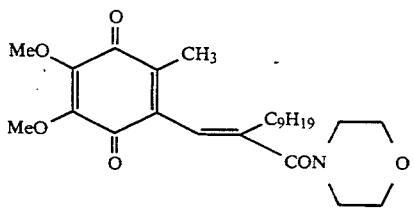

0.93 g of N-[(E)-3-[5-(6-methyl-1-methoxymethyloxy-2,3,4-trimethoxy)phenyl]-2-nonyl-2-propenoyl]morpholine prepared in Example 5 was dissolved in 10 ml of ethyl acetate and 10 g of ferric chloride hexahydrate was added thereto. The mixture was stirred at room temperature for 8 hr and 100 ml of water was added thereto. The organic phase was washed with water and dried over anhydrous magnesium sulfate. The solvent was distilled off, and the residue was purified by silica gel chromatography (eluent; n-hexane:ethyl acetate=1:2) to prepare 0.75 g of the product compound as an orange oleaginous substance.

$^1$H-NMR (δ): 0.86 (t, J=6 Hz, 3H), 1.00–1.50 (m, 14H), 1.94 (q, J=2 Hz, 3H), 2.00–2.20 (m, 2H), 3.50–3.80 (m, 8H), 3.96 (s, 3H), 3.98 (s, 3H), 5.88 (bs, 1H)

Compound Nos. 238 to 245 were prepared in the same manner as that of Example 6.

EXAMPLE 7

N-[(E)-3-5-(6-Methyl-1-methoxymethyloxy-2,3,4-trimethoxy)phenyl]-2-benzyl-2-propenoyl]-N'-methylpiperazine

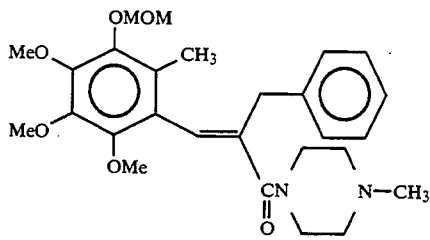

1.0 g of (E)-3-[5-(6-methyl-1-methoxymethyloxy-2,3,4-trimethoxy)phenyl]-2-benzyl-2-propenoic acid prepared in the same manner as that of Examples 1 and 2 and 1.0 ml of triethylamine were dissolved in 20 ml of THF, and 0.50 ml of diethylphosphonic acid chloride was dropwise added thereto and cooled by ice while stirring After the mixture was stirred at room temperature for 30 min, 1.0 ml of N-methylpiperazine was added thereto, and the mixture was stirred for 2 hr. Water was added to the reaction mixture, and the resulting mixture was extracted with ethyl acetate. The organic phase was washed with water and dried over anhydrous magnesium sulfate. The solvent was distilled off, and the residue was purified by silica gel column chromatography (eluent; chloroform:ethanol=95:5) to prepare 0.92 g of the product compound as a colorless oleaginous substance.

$^1$H-NMR (δ): 1.70–2.30 (m, 4H), 2.12 (s, 3H), 2.14 (s, 3H), 3.44 (s, 2H), 3.30–3.60 (m, 4H), 3.56 (s, 3H), 3.72 (s, 3H), 3.92 (s, 3H), 3.94 (s, 3H), 5.04 (s, 2H), 6.16 (s, 1H), 6.96–7.20 (m, 5H)

EXAMPLE 8

N(E)-3-[-5-(1-Hydroxy-6-methyl-2,3,4-trimethoxy)-phenyl]-2-benzyl-2-propenoyl]-N'-methylpiperazine hydrochloride

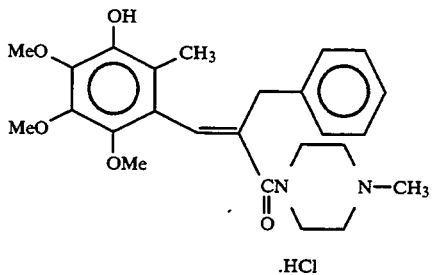

0.92 g of N-[(E)-3-[5-(6-methyl-1-methoxymethyloxy-2,3,4-trimethoxy)phenyl]-2-benzyl-2-propenoyl]-N'-methylpiperazine prepared in Example 7 was dissolved in 10 ml of acetone and 2 ml of 6N hydrochloric acid, and the resultant solution was stirred at 70° C. for 30 min. The solvent was distilled off in vacuo, and water was distilled off as an azeotrope with toluene to prepare 0.91 g of the product compound as a colorless amorphous substance.

$^1$H-NMR (δ): 2.04 (s, 3H), 2.70 (s, 3H), 3.00–3.30 (m, 4H), 3.30–3.60 (m, 4H), 3.36 (s, 2H), 3.69 (s, 3H), 3.84 (s, 3H), 3.88 (s, 3H), 6.36 (s, 1H), 6.90–7.30 (m, 5H)

EXAMPLE 9

(E)-3-[5-(2,3-Dimethoxy-6-methyl-1,4-benzoquinoyl)]-2-(3-methylsulfoxyl)propyl-2-propenoic acid

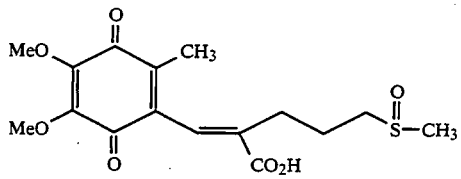

1.8 g of (E)-3-[5-(2,3-dimethoxy-6-methyl-1,4-benzoquinoyl)]-2-(3-methylsulfoxyl)propyl-2-propenoic acid (compound No. 183) prepared in the same manner as that of Examples 1 to 4 was dissolved in 50 ml of dichloromethane. The resultant solution was cooled to −30° C., and 1.0 g of m-chloroperbenzoic acid was added thereto in small portions while stirring. The mixture was stirred at −30° C. for an additional 30 min, and water was added thereto. The organic phase was washed with water and then dried over anhydrous magnesium sulfate. The solvent was distilled off, and the residue was purified by silica gel column chromatography (eluent; chloromethane:methanol= 90:10) to prepare 1.5 g of the product compound as an orange solid.

$^1$H-NMR (δ): 1.60–1.85 (m, 2H), 1.94 (s, 3H), 1.90–2.60 (m, 4H), 2.56 (s, 3H), 3.92 (s, 3H), 3.96 (s, 3H), 7.10 (s, 1H)

EXAMPLE 10

(E)-3-[5-(3-Ethoxy-2-methoxy-6-methyl-1,4-hydroquinoyl)]-2-cyclohexylmethyl-2-propenoic acid

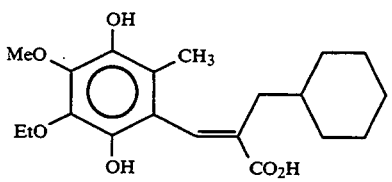

1.0 of (E)-3-[5-(3-ethoxy-2-methoxy-6-methyl-1,4-benzoquinoyl)]-2-cyclohexylmethyl-2-propenoic acid (compound No. 159) prepared in the same manner as that of Examples 1 to 4 was dissolved in 50 ml of ethyl acetate, and 10 g of sodium hydrosulfite in 100 ml of water was added thereto. The mixture was transferred to a separatory funnel and vigorously shaken. Phase separation was conducted when a red organic phase turned colorless. The organic phase was washed with water and dried over anhydrous magnesium sulfate. The solvent was distilled off to prepare 1.0 g of the product compound as a white solid.

$^1$H-NMR (δ): 0.40–1.86 (m, 11H), 1.38 (t, J=7 Hz, 3H), 2.08 (s, 3H), 2.01–2.17 (m, 2H), 3.86 (s, 3H), 4.06 (q, J=7 Hz, 2H), 7.56 (s, 1H)

Compounds No. 125 to 128 were prepared in the same manner as that of Example 10.

EXAMPLE 11

Ethyl(E)-3-[5-(3-ethoxy-2-methoxy-6-methyl-1,4benzoquinoyl)]-2-cyclohexylmethyl-2-propenoate

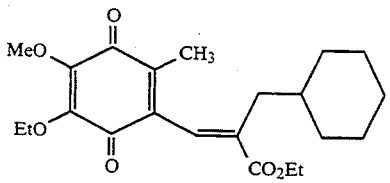

2.0 g of ethyl(E)-3-[5-(2,4-dimethoxy-3-ethoxy-1-methoxymethyloxy-6-methyl)phenyl]-2-cyclohexylmethyl-2-propenoate (compound No. 123) prepared in the same manner as that of Example 1 was dissolved in 50 ml of ethyl acetate, and 20 g of ferric chloride hexahydrate was added thereto. After the mixture was stirred at room temperature for 10 hr, 100 ml of ethyl acetate and 100 ml of water were added thereto, and the organic phase was washed with water and dried over anhydrous magnesium sulfate. The solvent was distilled off, and the residue was purified by silica gel column chromatography (eluent; n-hexane:ethyl acetate=9:1) to prepare 1.4 g of the product compound as an orange oleaginous substance.

$^1$H-NMR ($\delta$): 0.51–1.83 (m, 11H), 1.33 (t, J=7 Hz, 3H), 1.37 (t, J=7 Hz, 3H), 1.93 (d, J=2 Hz, 3H), 1.91–2.07 (m, 2H), 4.04 (s, 3H), 4.20 (q, J=7 Hz, 2H), 4.23 (q, J=7 Hz, 2H), 7.17 (bs, 1H)

Compound No. 246 was prepared in the same manner as that of Example 11.

EXAMPLE 12

(E)-3-[5-(1,4-Diacetoxy-3-ethoxy-2-methoxy-6-methyl)-phenyl]-2-cyclohexylmethyl-2-Propenoic acid (compound No. 145)

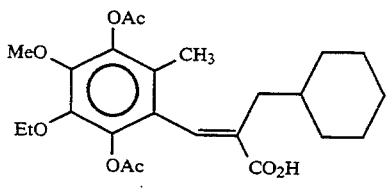

1.0 g of (E)-3-[5-(3ethoxy-2-methoxy-6-methyl-1,4-hydroquinoyl)]-2-cyclohexylmethyl-2-Propenoic acid prepared in Example 10 was dissolved in 10 ml of pyridine, and 2 ml of acetic anhydride was added thereto. After the mixture was stirred at room temperature for 1 hr, ice water was added thereto, and the mixture was stirred for 30 min, weakly acidified with 6N hydrochloric acid and extracted with ethyl acetate. The extract was washed with water and dried over anhydrous magnesium sulfate. The solvent was distilled off, and the residue was purified by silica gel column chromatography (eluent; chloroform:ethanol=95:5 ) to prepare 1.2 g of the product compound as a light yellow amorphous substance.

$^1$H-NMR ($\delta$): 0.40–1.86 (m, 11H), 1.31 (t, J=7 Hz, 3H), 1.98 (s, 3H), 2.01–2.17 (m, 2H), 2.23 (s, 3H), 2.34 (s, 3H), 3.86 (s, 3H), 4.04 (q, J=7 Hz, 2H) , 7.39 (bs, 1H)

Compound No. 129 was prepared in the same manner as that of Example 12.

EXAMPLE 13

Ethyl(Z)-3-[5-(6-methyl-1-methoxmethyloxy-2,3,4-trimethoxy)phenyl]-2-phenyl-2-propenoate

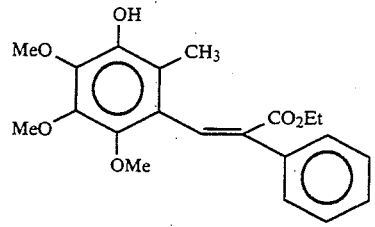

0.69 g of sodium hydride (60% oil suspension) was suspended in 15 ml of DMF, and 7.0 g of ethyl diethyl-phosphono-2-phenylacetate was dropwise added thereto at room temperature. After the reaction mixture became homogeneous, 3.15 g of 5-methoxymethyloxy-6-methyl-2,3,4-trimethoxybenzaldehyde (compound No. (1)) was dropwise added thereto at room temperature, and the reaction was allowed to proceed at 150° C. for 5 hr. The reaction mixture was poured into ice water and extracted with ethyl acetate. The organic phase was washed with water and dried over anhydrous magnesium sulfate, and the solvent was distilled off. The residue was purified by silica gel column chromatography (eluent; n-hexane:ethyl acetate=90:10), thereby obtaining first 1.8 g of the E isomer and then 1.0 g of the intended Z isomer as a colorless oil.

$^1$N-NMR ($\delta$): 1.00 (t, J=7.5 Hz, 3H), 2.17 (s, 3H), 3.56 (s, 3H), 3.69 (s, 3H), 3.86 (s, 6H), 4.06 (q, J=7.5 Hz, 2H), 5.01 (s, 2H), 6.86 (s, 1H), 7.11–7.53 (m, 5H)

EXAMPLE 14

(Z)-3-[5-(1-Hydroxy-6-methyl-2,3,4-trimethoxy)-phenyl]-2-phenyl-2-propenoic acid

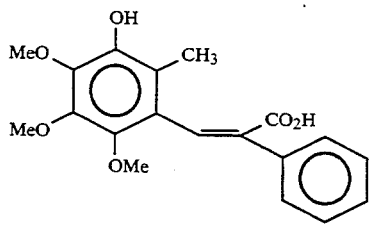

1 g of ethyl (Z)-3-[5-(6-methyl-1-methoxymethyloxy-2,3,4-trimethoxy)phenyl]-2-phenyl-2-propenoate prepared in Example 13 was hydrolyzed with sodium hydroxide in the same manner as that of Example 2 and then demethoxymethylated in acetone/6N hydrochloric acid in the same manner as that of Example 3 to prepare 0.5 g of the product compound as a white solid.

$^1$N-NMR ($\delta$): 2.14 (s, 3H), 3.70 (s, 3H), 3.85 (s, 3H), 3.96 (s, 3H), 6.90 (s, 1H), 7.17–7.57 (m, 5H)

EXAMPLE 15

Compounds listed in the following Tables 4 and 5 were prepared according to the methods described in Examples 1 to 14.

Hydroquinone compounds (compound No. 1 to 129) and quinone compounds (compound No. 130 to 246 ) are listed in Tables 4 and 5, respectively.

TABLE 4

[Structure: benzene ring with substituents R³, R⁴, R⁵, X, Y and a side chain -C(R¹)=CH- connected to -C(=O)-R²]

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 1 | MeO | MeO | Me | MOMO | MeO | Cyclohexyl-CH₂ | OEt | colorless oil | 0.50–1.70(m, 11H), 1.35(t, J=7Hz, 3H), 2.08(s, 3H) 2.00–2.20(m, 2H), 3.56(s, 3H), 3.70(s, 3H), 3.86 (s, 3H), 3.88(s, 3H), 4.14(q, J=7Hz, 2H), 5.04(s, 2H), 7.38(s, 1H) |
| 2 | EtO | EtO | Me | MOMO | EtO | Cyclohexyl-CH₂ | OEt | colorless oil | 0.40–2.00(m, 11H), 1.26(t, J=7Hz, 3H), 1.35(t, J=7Hz, 3H), 1.38(t, J=7Hz, 3H), 1.40(t, J=7Hz, 3H), 2.08(s, 3H), 2.00–2.20(m, 2H), 3.56(s, 3H), 3.84(q, J=7Hz, 2H), 4.10(q, J=7Hz, 2H), 4.14(q, J=7Hz, 2H), 4.22(q, J=7Hz, 2H), 5.04(s, 2H), 7.35(s, 1H) |
| 3 | MeO | EtO | Me | MOMO | MeO | Cyclohexyl-CH₂ | OEt | colorless oil | 0.54–1.77(m, 11H), 1.34(t, J=7Hz, 3H), 1.39(t, J=7Hz, 3H), 2.03–2.14(m, 2H), 2.11(s, 3H), 3.60(s, 3H), 3.73(s, 3H), 3.93(s, 3H), 4.09(q, J=7Hz, 2H), 4.27(q, J=7Hz, 2H), 5.09(s, 2H), 7.46(bs, 1H) |
| 4 | MeO | MeO | Me | MOMO | MeO | ⁻(CH₂)₄CN | OEt | colorless oil | 1.36(t, J=7Hz, 3H), 1.40–1.60(m, 4H), 2.08(s, 3H) 2.05–2.30(m, 4H), 3.56(s, 3H), 3.68(s, 3H), 3.90 (s, 6H), 4.18(q, J=7Hz, 2H), 5.04(s, 2H), 7.40(s, 1H) |
| 5 | MeO | EtO | Me | MOMO | MeO | -CH₂CH₂CH(CH₃)-CH₃ | OEt | colorless oil | 0.72(d, J=6Hz, 6H), 1.20–1.50(m, 3H), 1.34(q, J=7Hz, 3H), 1.38(q, J=7Hz, 3H), 2.08(s, 3H), 2.05–2.25(m, 2H), 3.56(s, 3H), 3.70(s, 3H), 3.88(s, 3H), 4.06(q, J=7Hz, 2H), 4.27(q, T=7Hz, 2H), 5.04(s, 2H), 7.50(s, 1H) |
| 6 | MeO | MeO | Me | MeO | MOMO | -CH₂CH₂CH(CH₃)-CH₃ | OEt | colorless oil | 0.77(d, J=6Hz, 6H), 1.14–1.69(m, 3H), 1.31(t, J=7Hz, 3H), 2.09–2.40(m, 2H), 3.47(s, 3H), 3.69(s, 3H), 3.83(s,3H), 3.84(s, 3H), 3.93(s, 3H), 4.23(q, J=7Hz, 2H), 4.94(s, 2H), 7.37(s, 1H) |
| 7 | MeO | MeO | Me | MOMO | MeO | ⁻(CH₂)₃S-Me | OEt | colorless oil | 1.36(t, J=7Hz, 3H), 1.50–1.85(m, 2H), 1.96(s, 3H), 2.08(s, 3H), 2.05–2.25(m, 4H), 3.56(s, 3H), 3.70 (s, 3H), 3.88(s, 6H), 4.24(q, J=7Hz, 2H), 5.06(s, 2H), 7.40(s, 1H) |

TABLE 4-continued

Structure: phenyl ring with substituents X, Y, R³, R⁴, R⁵ and a CR¹=CH-C(=O)-R² side chain

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 8 | MeO | MeO | Me | MOMO | MeO | −CH₂−(2-thienyl) | OEt | colorless oil | 1.28(t, J=7Hz, 3H), 2.06(s, 3H), 3.56(s, 3H), 3.68(s, 3H), 3.72(s, 2H), 3.90(s, 6H), 4.20(q, J=7Hz, 2H), 5.02(s, 2H), 6.50−7.05(m, 3H), 7.45(s, 1H) |
| 9 | MeO | MeO | Me | MOMO | MeO | −CH₂−cyclohexyl | OH | colorless oil | 0.50−1.70(m, 11H), 2.04(s, 3H), 2.00−2.20(m, 2H), 3.56(s, 3H), 3.68(s, 3H), 3.88(s, 3H), 3.96(s, 3H), 5.04(s, 2H), 7.00(s, 1H) |
| 10 | EtO | EtO | Me | MOMO | MeO | −CH₂−cyclohexyl | OH | colorless oil | 0.40−2.00(m, 11H), 1.26(t, J=7Hz, 3H), 1.38(t, J=7Hz, 3H), 1.40(t, J=7Hz, 3H), 2.00−2.20(m, 2H), 3.56(s, 3H), 3.84(q, J=7Hz, 2H), 4.10(q, J=7Hz, 2H), 4.22(q, J=7Hz, 2H), 5.04(s, 2H), 7.36(s, 1H) |
| 11 | MeO | EtO | Me | MOMO | EtO | −CH₂−cyclohexyl | OH | colorless oil | 0.46−1.71(m, 11H), 1.40(t, J=7Hz, 3H), 2.11(s, 3H), 2.11−2.17(m, 2H), 3.60(s, 3H), 3.74(s, 3H), 3.93(s, 3H), 4.09(q, J=7Hz, 2H), 5.09(s, 2H), 7.63(bs, 1H) |
| 12 | MeO | MeO | Me | MOMO | MeO | −(CH₂)₇−CN | OH | colorless oil | 1.40−1.80(m, 4H), 2.08(s, 3H), 2.05−2.30(m, 4H), 3.56(s, 3H), 3.08(s, 3H), 3.90(s, 3H), 3.98(s, 3H), 5.09(s, 2H), 7.60(s, 1H) |
| 13 | MeO | EtO | Me | MOMO | MeO | −CH₂CH₂CH(CH₃)−CH₃ | OH | colorless oil | 0.72(d, J=6Hz, 6H), 1.20−1.50(m, 3H), 1.38(q, J=7Hz, 3H), 2.08(s, 3H), 2.05−2.25(m, 2H), 3.56(s, 3H), 3.70(s, 3H), 3.88(s, 3H), 4.06(q, J=7Hz, 2H), 5.04(s, 2H), 7.50(s, 1H) |
| 14 | MeO | MeO | Me | MeO | MOMO | −CH₂CH₂CH(CH₃)−CH₃ | OH | colorless oil | 0.76(d, J=6Hz, 6H), 1.11−1.69(m, 3H), 2.11−2.40(m, 2H), 3.47(s, 3H), 3.71(s, 3H), 3.83(s, 3H), 3.86(s, 3H), 3.93(s, 3H), 4.96(s, 2H), 7.54(s, 1H) |
| 15 | MeO | MeO | Me | MeO | MOMO | −(CH₂)₃−SMe | OH | colorless oil | 1.50−1.85(m, 2H), 1.96(s, 3H), 2.08(s, 3H), 2.05−2.25(m, 4H), 3.56(s, 3H), 3.70(s, 3H), 3.90(s, 3H), 3.94(s, 3H), 5.04(s, 2H), 7.38(s, 1H) |

TABLE 4-continued

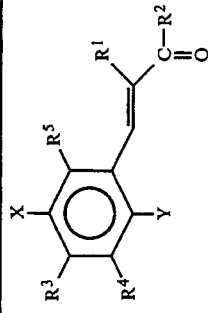

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 16 | MeO | MeO | Me | MOMO | MeO | —CH₂— (thienyl) | OH | colorless oil | 2.06(s, 3H), 3.58(s, 3H), 3.70(s, 3H), 3.74(s, 2H), 3.40(s, 6H), 5.04(s, 2H), 6.60–7.08(m, 3H), 7.65 (s, 1H) |
| 17 | EtO | MeO | Me | OH | MeO | Et | OH | white solid 114–116° C. | 0.96(t, J=7Hz, 3H), 2.06(s, 3H), 2.16(q, J=7Hz, 2H), 3.64(s, 3H), 3.88(s, 3H), 3.92(s, 3H), 7.32(s, 1H) |
| 18 | EtO | EtO | Me | OH | EtO | Et | OH | white solid 100–102° C. | 1.00(t, J=7Hz, 3H), 1.28(t, J=7Hz, 3H), 1.40(t, J=7Hz, 6H), 2.06(s, 3H), 2.22(q, J=7Hz, 2H), 3.84(q, J=7Hz, 2H), 4.10(q, J=7Hz, 2H), 4.23(q, J=7Hz, 2H), 7.56(s, 1H) |
| 19 | MeO | MeO | Me | OH | MeO | ⁺(CH₂)₇CH₃ | OH | white solid 100–102° C. | 0.77(t, J=6Hz, 3H), 1.00–1.80(m, 6H), 2.04(s, 3H), 2.00–2.30(m, 2H), 3.64(s, 3H), 3.88(s, 3H), 3.92 (s, 3H), 7.52(s, 1H), |
| 20 | EtO | EtO | Me | OH | EtO | ⁺(CH₂)₇CH₃ | OH | white solid 88–90° C. | 0.80(t, J=6Hz, 3H), 1.27(t, J=7Hz, 3H), 1.05–1.60 (m, 6H), 1.38(t, J=7Hz, 3H), 1.40(t, J=7Hz, 3H), 2.06(s, 3H), 2.00–2.30(m, 2H), 3.85(q, J=7Hz, 2H), 4.10(q, J=7Hz, 2H), 4.22(q, J=7Hz, 2H), 7.58(s, 1H) |
| 21 | MeO | MeO | Me | OH | MeO | —CH₂CH₂CH—CH₃ (CH₃) | OH | white solid 75–77° C. | 0.73(d, J=6Hz, 6H), 1.10–1.40(m, 3H), 2.08(s, 3H), 2.00–2.20(m, 2H), 3.68(s, 3H), 3.90(s, 3H), 3.94 (s, 3H), 7.35(s, 1H) |
| 22 | MeO | EtO | Me | OH | MeO | —CH₂CH₂CH—CH₃ (CH₃) | OH | colorless oil | 0.72(d, J=6Hz, 6H), 1.20–1.50(m, 3H), 1.38(t, J=7Hz, 3H), 2.08(s, 3H), 2.05–2.25(m, 2H), 3.70(s, 3H), 3.88(s, 3H), 4.06(q, J=7Hz, 2H), 7.50(s, 1H) |
| 23 | EtO | EtO | Me | OH | EtO | —CH₂CH₂CH—CH₃ (CH₃) | OH | white solid 101–103° C. | 0.72(d, J=6Hz, 6H), 1.26(t, J=7Hz, 3H), 1.36(t, J=7Hz, 3H), 1.38(t, J=7Hz, 3H), 1.20–1.60(m, 3H), 2.08(s, 3H), 2.05–2.20(m, 2H), 3.86(q, J=7Hz, 2H), 4.06(q, J=7Hz, 2H), 4.12(q, J=7Hz, 2H), 7.36(s, 1H) |
| 24 | MeO | MeO | MeO | MeO | OH | —CH₂CH₂CH—CH₃ (CH₃) | OH | white solid 130–131° C. | 0.79(d, J=6Hz, 6H), 1.14–1.66(m, 3H), 2.11–2.44 (m, 2H), 3.77(s, 3H), 3.86(s, 3H), 3.91(s, 3H), 3.97 (s, 3H), 7.57(s, 3H) |
| 25 | MeO | MeO | Me | OH | MeO | (cyclopentyl) | OH | white solid 129° C. | 1.38–1.94(m, 8H), 2.07(s, 3H), 2.40–2.80(m, 1H), 3.68(s, 3H), 3.91(s, 3H), 3.97(s, 3H), 7.55(s, 1H) |

TABLE 4-continued

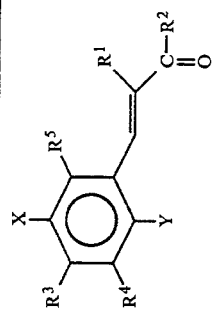

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 26 | EtO | EtO | Me | OH | EtO | (methylcyclopentyl) | OH | white solid 141° C. | 1.28(t, J=7Hz, 3H), 1.38(t, J=7Hz, 3H), 1.39(t, J=7Hz, 3H), 1.50–1.92(m, 8H), 2.06(s, 3H), 2.40–2.82 (m, 1H), 3.80(q, J=7Hz, 2H), 4.07(q, J=7Hz, 2H), 4.19(q, J=7Hz, 2H), 7.51(s, 1H) |
| 27 | MeO | MeO | Me | OH | MeO | —CH₂(cyclopentyl) | OH | colorless oil | 0.80–1.70(m, 9H), 2.12(s, 3H), 2.00–2.30(m, 2H), 3.68(s, 3H), 3.90(s, 3H), 3.94(s, 3H), 7.38(s, 1H) |
| 28 | MeO | MeO | Me | OH | MeO | CH₂(cyclohexyl) | OH | colorless oil | 0.58–1.70(m, 11H), 2.04(s, 3H), 2.00–2.20(m, 2H), 3.68(s, 3H), 3.88(s, 3H), 3.96(s, 3H), 7.60(s, 1H) |
| 29 | MeO | EtO | Me | OH | MeO | CH₂(cyclohexyl) | OH | colorless oil | 0.46–1.77(m, 11H), 1.37(t, J=7Hz, 3H), 2.04(s, 3H), 2.04–2.23(m, 2H), 3.67(s, 3H), 3.97(s, 3H), 4.09 (q, J=7Hz, 2H), 7.63(s, 1H) |
| 30 | EtO | MeO | Me | OH | EtO | CH₂(cyclohexyl) | OH | white solid 154° C. | 0.50–1.80(m, 11H), 1.28(t, J=7Hz, 3H), 1.40(t, J=7Hz, 3H), 2.20–2.28(m, 2H), 2.08(s, 3H), 3.84(q, J=7Hz, 2H), 4.23(q, J=7Hz, 2H), 7.62(s, 1H) |
| 31 | EtO | EtO | Me | OH | EtO | CH₂(cyclohexyl) | OH | colorless oil | 0.40–2.00(m, 11H), 1.26(t, J=7Hz, 3H), 1.38(t, J=7Hz, 3H), 1.40(t, J=7Hz, 3H), 2.08(s, 3H), 2.00–2.20(m, 2H), 3.84(q, J=7Hz, 2H), 4.10(q, J=7Hz, 2H), 4.22(q, J=7Hz, 2H), 7.36(s, 1H) |

TABLE 4-continued structure

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 32 | MeO | n-PrO | Me | OH | MeO | CH₂-cyclohexyl | OH | colorless oil | 0.49–2.24(m, 18H), 2.04(s, 3H), 3.67(s, 3H), 3.97 (s, 3H), 3.97(q, J=7Hz, 2H), 7.61(s, 1H) |
| 33 | MeO | iso-PrO | Me | OH | MeO | CH₂-cyclohexyl | OH | colorless oil | 0.49–2.37(m, 13H), 1.30(d, J=6Hz, 6H), 2.06(s, 3H), 3.70(s, 3H), 3.97(s, 3H), 4.46(hept, J=6Hz, 1H), 7.67(bs, 1H) |
| 34 | MeO | 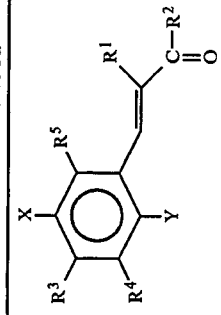 | Me | OH | MeO | CH₂-cyclohexyl | OH | slightly yellow oil | 0.57–2.11(m, 22H), 2.21(s, 3H), 3.06(s, 3H), 3.67 (s, 2H), 3.83(s, 2H), 3.94(s, 3H), 7.61(bs, 1H) |
| 35 | MeO | H | MeO | MeO | OH | CH₂-cyclohexyl | OH | slightly yellow oil | 0.40–1.80(m, 11H), 2.07–2.27(m, 2H), 3.76(s, 3H), 3.83(s, 3H), 3.84(s, 3H), 6.26(s, 1H), 7.56(s, 1H) |
| 36 | MeO | MeO | MeO | MeO | OH | CH₂-cyclohexyl | OH | colorless oil | 0.39–1.86(m, 11H), 2.14–2.34(m, 2H), 3.77(s, 3H), 3.85(s, 3H), 3.91(s, 3H), 3.99(s, 3H), 7.63(s, 1H) |
| 37 | MeO | MeO | OH | MeO | MeO | —(CH₂)₇— | OH | slightly yellow oil | 0.66–2.26(m, 17H), 2.04(s, 3H), 3.64(s, 3H), 3.87 (s, 3H), 3.94(s, 3H), 7.51(s, 1H) |
| 38 | MeO | MeO | Me | OH | MeO | ⁺(CH₂)₇CH₃ | OH | colorless oil | 0.69–1.51(m, 15H), 2.00–2.26(m, 2H), 2.04(s, 3H), 3.66(s, 3H), 3.90(s, 3H), 3.96(s, 3H), 7.56(s, 1H) |
| 39 | MeO | EtO | Me | OH | MeO | ⁺(CH₂)₇CH₃ | OH | colorless oil | 0.71–1.54(m, 15H), 1.33(t, J=7Hz, 3H), 2.00–2.29 (m, 2H), 2.04(s, 3H), 3.66(s, 3H), 3.96(s, 3H), 4.10 |

TABLE 4-continued

![Structure: benzene ring with substituents X, R³, R⁴, R⁵, Y, and a vinyl group with R¹ and C(=O)R²]

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 40 | MeO | EtO | Me | OH | MeO | ─(CH₂)₈─CH₃ | OH | colorless oil | (q, J=7Hz, 2H), 7.54(bs, 1H) 0.86(t, J=7Hz, 3H), 1.04–1.59(m, 14H), 1.39(t, J=7Hz, 3H), 2.00–2.28(m, 2H), 2.03(s, 3H)3.63(s, 3H) 3.93(s, 3H), 4.08(q, J=7Hz, 2H), 7.53(s, 1H) |
| 41 | EtO | MeO | Me | OH | EtO | ─(CH₂)₈─CH₃ | OH | colorless oil | 0.86(t, J=7Hz, 3H), 1.03–1.60(m, 14H), 1.28(t, J=7Hz, 3H), 1.40(t, J=7Hz, 3H), 1.99–2.30(m, 2H), 2.05(s, 3H), 3.82(q, J=7Hz, 2H), 3.88(s, 3H), 4.18 (q, J=7Hz, 2H), 7.54(s, 1H) |
| 42 | EtO | EtO | Me | OH | EtO | ─(CH₂)₈─CH₃ | OH | colorless oil | 0.86(t, J=6Hz, 3H), 1.02–1.60(m, 14H), 1.27(t, J=7Hz, 3H), 1.38(t, J=7Hz, 3H), 1.39(t, J=7Hz, 3H), 2.00–2.29(m, 2H), 2.04(s, 3H), 3.82(q, J=7Hz, 2H), 4.08 (q, J=7Hz, 2H), 4.20(q, J=7Hz, 2H), 7.53(s, 1H) |
| 43 | MeO | MeO | MeO | MeO | OH | ─(CH₂)₈─CH₃ | OH | colorless oil | 0.69–1.74(m, 17H), 2.11–2.60(m, 2H), 3.73(s, 3H), 3.83(s, 3H), 3.87(s, 3H), 3.94(s, 3H), 7.50(s, 1H) |
| 44 | MeO | MeO | Me | OH | MeO | ─(CH₂)₇─C=C─CH₂CH₃ (H, H) | OH | colorless oil | 0.92(t, 7Hz, 3H), 1.04–1.57(m, 6H), 1.72–2.32(m, 6H), 2.06(s, 3H), 3.67(s, 3H), 3.90(s, 3H), 3.97(s, 3H), 5.16–5.40(m, 2H), 7.57(s, 1H) |
| 45 | MeO | MeO | Me | OH | MeO | ─(CH₂CH₂CH─CH₂)₂H (CH₃) | OH | colorless oil | 0.60–1.40(m, 13H), 1.82(d, J=6Hz, 6H), 2.00–2.25 (m, 2H), 2.08(s, 3H), 3.70(s, 3H), 3.90(s, 3H), 3.94 (s, 3H), 7.34(s, 1H) |
| 46 | MeO | MeO | Me | OH | MeO | ─CH₂CH₂CCH₂CH₂CH=C(CH₃)₂ (CH₃, H) | OH | colorless oil | 0.70(d, J=6Hz, 3H), 0.90–1.50(m, 5H), 1.55(s, 3H), 1.65(s, 3H), 1.70–2.30(m, 4H), 2.06(s, 3H), 3.65 (s, 3H), 3.89(s, 3H), 3.96(s, 3H), 4.84–5.10(m, 1H) 7.54(s, 1H) |
| 47 | MeO | MeO | Me | OH | MeO | ─(CH₂)₇─CH₃ | OH | colorless oil | 0.87(t, J=6Hz, 3H), 1.00–1.58(m, 16H), 2.05(s, 3H), 1.96–2.27(m, 2H), 3.66(S, 3H), 3.89(s, 3H), 3.96 (s, 3H), 7.53(s, 1H) |
| 48 | MeO | MeO | Me | OH | MeO | ─(CH₂)₁₀─CH₃ | OH | colorless oil | 0.87(t, J=6Hz, 3H), 1.00–1.57(m, 18H), 2.04(s, 3H) 2.00–2.26(m, 2H), 3.66(S, 3H), 3.89(s, 3H), 3.94 (s, 3H), 7.54(bs, 1H) |
| 49 | MeO | MeO | Me | OH | MeO | ─(CH₂)₁₁─CH₃ | OH | colorless oil | 0.87(t, J=6Hz, 3H), 1.00–1.69(m, 20H), 2.04(s, 3H), 2.00–2.26(m, 2H), 3.66(S, 3H), 3.89(s, 3H), 3.96 (s, 3H), 7.55(bs, 1H) |
| 50 | MeO | MeO | Me | OH | MeO | ─(CH₂)₇─C≡CH | OH | white solid 88° C. | 1.54–1.92(m, 2H), 1.79(t, J=2Hz, 1H), 1.94–2.42 (m, 4H), 2.08(s, 3H), 3.69(s, 3H), 3.89(s, 3H), 3.97 (s, 3H), 7.59(s, 1H) |

TABLE 4-continued

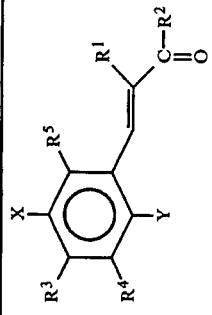

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 51 | MeO | EtO | Me | OH | MeO | ⁺(CH₂)₃C≡CH | OH | white solid 92° C. | 1.39(t, J=7Hz, 3H), 1.50-1.72(m, 2H), 1.79(t, J=2Hz, 1H), 1.93-2.40(m, 4H), 2.03(s, 3H), 3.67(s, 3H), 3.95(s, 3H), 4.09(q, J=7Hz, 2H), 7.60(s, 1H) |
| 52 | EtO | EtO | Me | OH | EtO | ⁺(CH₂)₃C≡CH | OH | white solid 75° C. | 1.27(t, J=7Hz, 3H), 1.37(t, J=7Hz, 3H), 1.38(t, J=7Hz, 3H), 1.50-1.84(m, 2H), 1.79(t, J=2Hz, 1H), 1.90-2.42(m, 4H), 2.08(s, 3H), 3.81(q, J=7Hz, 2H), 4.06(q, J=7Hz, 2H), 4.19(q, J=7Hz, 2H), 7.59(s, 1H) |
| 53 | MeO | MeO | Me | OH | MeO | —CH₂CN | OH | colorless oil | 2.14(s, 3H), 3.22(s, 2H), 3.70(s, 3H), 3.90(s, 6H), 7.64(s, 1H) |
| 54 | EtO | EtO | Me | OH | EtO | —CH₂CN | OH | colorless oil | 1.30(t, J=7Hz, 3H), 1.42(t, J=7Hz, 6H), 2.16(s, 3H), 3.24(s, 2H), 3.86(q, 7Hz, 2H), 4.10(q, J=7Hz, 2H), 4.35(q, J=7Hz, 2H), 7.64(s, 1H) |
| 55 | MeO | MeO | Me | OH | MeO | ⁺(CH₂)₃CN | OH | white solid 131-133° C. | 1.80-2.00(m, 2H), 2.06(s, 3H), 2.00-2.40(m, 4H), 3.68(s, 3H), 3.90(s, 3H), 3.98(s, 3H), 7.60(s, 1H) |
| 56 | MeO | EtO | Me | OH | MeO | ⁺(CH₂)₃CN | OH | white solid 109-110° C. | 1.40(t, J=7Hz, 3H), 1.66-2.43(m, 6H), 1.99(d, J=2Hz, 3H), 3.70(s, 3H), 4.03(s, 3H), 4.27(q, J=7Hz, 2H), 7.43(bs, 1H) |
| 57 | EtO | MeO | Me | OH | EtO | ⁺(CH₂)₃CN | OH | white solid 119° C. | 1.28(t, J=7Hz, 3H), 1.40(t, J=7Hz, 3H), 1.62-2.00(m, 2H), 2.07(s, 3H), 2.05-2.50(m, 4H), 3.85(q, J=7Hz, 2H), 3.91(s, 3H), 4.23(q, J=7Hz, 2H), 7.70(s, 1H) |
| 58 | EtO | EtO | Me | OH | EtO | ⁺(CH₂)₃CN | OH | white solid 106-108° C. | 1.28(t, J=7Hz, 3H), 1.36(t, J=7Hz, 3H), 1.38(t, J=7Hz, 3H), 1.40-1.80(m, 2H), 2.08(s, 3H), 2.00-2.40(m, 4H), 3.84(q, J=7Hz, 2H), 4.08(q, J=7Hz, 2H), 4.26(q, J=7Hz, 2H), 7.40(s, 1H) |
| 59 | MeO | nPrO | Me | OH | MeO | ⁺(CH₂)₃CN | OH | white solid 95-97° C. | 1.06(t, J=7Hz, 3H), 1.63-2.49(m, 11H), 3.67(s, 3H), 3.96(s, 3H), 3.99(t, J=6Hz, 2H), 7.67(bs, 1H) |
| 60 | MeO | iso-PrO | Me | OH | MeO | ⁺(CH₂)₃CN | OH | white solid 102-121° C. | 1.30(d, J=6Hz, 6H), 1.59-2.86(m, 6H), 2.04(s, 3H), 3.67(s, 3H), 3.96(s, 3H), 4.43(hept, 6H, 1H), 7.66(bs, 1H) |
| 61 | MeO | n-OctO | Me | OH | MeO | ⁺(CH₂)₃CN | OH | white solid 101° C. | 0.90(t, J=6Hz, 3H), 1.18-1.60(m, 10H), 1.60-1.95(m, 4H), 2.06-2.42(m, 4H), 2.04(s, 3H), 3.68(s, 3H), 3.96(s, 3H), 4.00(t, J=7Hz, 2H), 7.66(s, 1H) |
| 62 | MeO | H | MeO | MeO | OH | ⁺(CH₂)₃CN | OH | colorless oil | 1.71-2.57(m, 6H), 6.24(s, 1H), 3.81(s, 3H), 3.83 (s, 3H) |
| 63 | MeO | MeO | Me | OH | MeO | ⁺(CH₂)₄CN | OH | colorless oil | 1.40-1.80(m, 4H), 2.06(s, 3H), 2.05-2.40(m, 4H), 3.68(s, 3H), 3.90(s, 3H), 3.98(s, 3H), 7.60(s, 1H) |
| 64 | MeO | EtO | Me | OH | MeO | ⁺(CH₂)₄CN | OH | light yellow oil | 1.40(t, J=7Hz, 3H), 1.40-1.63(m, 4H), 2.01-2.31 (m, 4H), 2.04(s, 3H), 3.66(s, 3H), 3.96(s, 3H), 4.07 (q, J=7Hz, 2H), 7.59(s, 1H) |
| 65 | EtO | MeO | Me | OH | EtO | ⁺(CH₂)₄CN | OH | light | 1.37(t, J=7Hz, 6H), 1.37-1.69(m, 4H), 2.00-2.31 |

TABLE 4-continued

Structure:
Phenyl ring with substituents X, Y, R³, R⁴, R⁵, and a vinyl group -C(R¹)=CH- attached to C(=O)-R²

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 66 | EtO | EtO | Me | OH | EtO | (CH₂)₄CN | OH | yellow oil | (m, 4H), 2.03(s, 3H), 3.86(s, 3H), 3.83(q, J=7Hz, 2H), 4.17(q, J=7Hz, 2H), 7.57(s, 1H) |
| 67 | MeO | MeO | MeO | MeO | OH | (CH₂)₄CN | OH | light yellow oil | 1.21(t, J=7Hz, 3H), 1.36(t, J=7Hz, 3H), 1.38(t, J=7Hz, 3H), 1.40-1.80(m, 4H), 2.08(s, 3H), 2.00-2.40(m, 4H), 3.84(q, J=7Hz, 2H), 4.08(q, J=7Hz, 2H), 4.26(q, J=7Hz, 2H), 7.40(s, 1H) |
| 68 | MeO | MeO | Me | OH | MeO | (CH₂)₈CN | OH | colorless oil | 1.50-1.86(m, 4H), 2.14-2.49(m, 4H), 3.79(s, 3H), 3.87(s, 3H), 3.93(s, 3H), 4.00(s, 3H), 7.63(s, 1H) |
| 69 | EtO | EtO | Me | OH | EtO | (CH₂)₈CN | OH | white solid 97° C. | 1.08-1.80(m, 12H), 2.06(s, 3H), 2.00-2.41(m, 4H), 3.68(s, 3H), 3.92(s, 3H), 3.98(s, 3H), 7.58(s, 1H) |
| 70 | MeO | MeO | Me | OH | MeO | (CH₂)₃SMe | OH | white solid 67° C. | 1.01-1.75(m, 12H), 1.28(t, J=7Hz, 3H), 1.39(t, J=7Hz, 3H), 1.40(t, J=7Hz, 3H), 1.98-2.40(m, 4H), 2.08(s, 3H), 3.84(q, J=7Hz, 2H), 4.10(q, J=7Hz, 2H), 4.24(q, J=7Hz, 2H), 7.59(s, 1H) |
| 71 | MeO | EtO | Me | OH | MeO | (CH₂)₃SMe | OH | colorless oil | 1.50-1.85(m, 2H), 1.96(s, 3H), 2.08(s, 3H), 2.05-2.25(m, 4H), 3.70(s, 3H), 3.90(s, 3H), 3.94(s, 3H), 7.38(s, 1H) |
| 72 | MeO | MeO | MeO | MeO | OH | (CH₂)₃SMe | OH | light yellow oil | 1.39(t, J=7Hz, 3H), 1.56-1.85(m, 2H), 1.96(s, 3H), 2.06(s, 3H), 2.18-2.45(m, 4H), 3.66(s, 3H), 3.97(s, 3H), 4.11(q, J=7Hz, 2H), 7.62(s, 1H) |
| 73 | MeO | MeO | Me | OH | MeO | (CH₂)₃S-cyclohexyl | OH | colorless oil | 1.71-1.94(m, 2H), 2.00(s, 3H), 2.29-2.54(m, 4H), 3.77(s, 3H), 3.86(s, 3H), 3.91(s, 3H), 3.97(s, 3H), 7.60(s, 1H) |
| 74 | MeO | EtO | Me | OH | MeO | (CH₂)₃S-cyclohexyl | OH | colorless oil | 1.10-2.00(m, 12H), 2.08(s, 3H), 2.10-2.50(m, 5H), 3.70(s, 3H), 3.90(s, 3H), 3.96(s, 3H), 7.40(s, 1H) |
|  |  |  |  |  |  |  |  | colorless oil | 1.07-1.96(m, 11H), 1.37(t, J=7Hz, 3H), 2.03(s, 3H), 2.14-2.46(m, 6H), 3.63(s, 3H), 3.93(s, 3H), 4.07(q, J=7Hz, 2H), 7.40(s, 1H) |

TABLE 4-continued

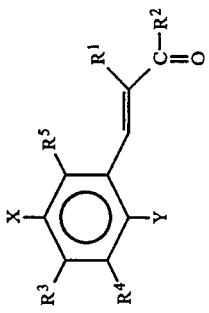

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 75 | MeO | MeO | MeO | MeO | OH | ‒(CH₂)₃S-cyclohexyl | OH | colorless oil | 1.00–2.09(m, 12H), 2.26–2.73(m, 5H), 3.77(s, 3H), 3.86(s, 3H), 3.91(s, 3H), 3.97(s, 3H), 7.61(s, 1H) |
| 76 | MeO | MeO | Me | OH | MeO | ‒CH₂-(tetrahydropyran) | OH | light yellow oil | 1.11–1.97(m, 6H), 2.03(s, 3H), 2.29–2.43(m, 2H), 3.17–3.57(m, 2H), 3.63(s, 3H), 3.86(s, 3H), 3.94(s, 3H), 3.94–4.11(m, 1H), 7.60(s, 1H) |
| 77 | MeO | MeO | Me | OH | MeO | ‒(CH₂CH₂O)₃Me | OH | light yellow oil | 2.04(s, 3H), 2.37–2.60(m, 2H), 3.34(s, 3H), 3.40–3.74(m, 10H), 3.06(s, 3H), 3.89(s, 3H), 3.93(s, 3H), 7.57(s, 1H) |
| 78 | MeO | MeO | Me | OH | MeO | ‒CH₂-phenyl | OH | colorless oil | 2.08(s, 3H), 3.58(s, 2H), 3.83(s, 3H), 3.88(s, 6H), 6.80–7.20(m, 5H), 7.65(s, 1H) |
| 79 | EtO | EtO | Me | OH | EtO | ‒CH₂-phenyl | OH | white solid 105–107° C. | 1.26(t, J=7Hz, 3H), 1.38(t, J=7Hz, 6H), 2.02(s, 3H), 3.56(s, 2H), 3.80(q, J=7Hz, 2H), 4.06(q, J=7Hz, 2H), 4.18(q, J=7Hz, 2H), 6.90–7.20(m, 5H), 7.66(s, 1H) |
| 80 | MeO | MeO | Me | OH | MeO | ‒CH₂-(4-F-phenyl) | OH | white solid 96–98° C. | 2.02(s, 3H), 3.52(s, 2H), 3.86(s, 3H), 3.92(s, 6H), 6.60–7.05(m, 4H), 7.66(s, 1H) |
| 81 | MeO | EtO | Me | OH | MeO | ‒CH₂-(4-F-phenyl) | OH | white solid 135–137° C. | 1.29(t, J=7Hz, 3H), 2.01(s, 3H), 3.50(bs, 2H), 3.64(s, 3H), 3.96(s, 3H), 4.06(q, J=7Hz, 2H), 6.66–7.06(m, 4H), 7.69(bs, 1H) |

TABLE 4-continued structure: benzene ring with substituents X, Y, R³, R⁴, R⁵, connected to C(R¹)=C–C(=O)–R²

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 82 | EtO | EtO | Me | OH | EtO | —CH₂—(4-F-C₆H₄) | OH | white solid 147–149° C. | 1.26(t, J=7Hz, 3H), 1.38(t, J=7Hz, 3H), 1.39(t, J=7Hz, 3H), 2.16(s, 3H), 3.52(s, 2H), 3.84(q, J=7Hz, 2H), 4.10(q, J=7Hz, 2H), 4.20(q, J=7Hz, 2H), 6.60–7.00(m, 4H), 7.66(s, 1H) |
| 83 | MeO | MeO | Me | OH | MeO | —CH₂—(4-CO₂H-C₆H₄) | OH | white solid 241° C. (decomp.) | 2.04(s, 3H), 3.60(s, 2H), 3.72(s, 3H), 3.86(s, 6H), 7.06(d, J=8Hz, 2H), 7.60(s, 1H), 7.82(d, J=8Hz, 2H) |
| 84 | EtO | EtO | Me | OH | EtO | —CH₂—(4-CO₂H-C₆H₄) | OH | white solid 238° C. (decomp.) | 1.38(t, J=7Hz, 3H), 1.48(t, J=7Hz, 6H), 2.08(s, 3H), 3.70(s, 2H), 3.88(q, J=7Hz, 2H), 4.18(q, J=7Hz, 2H), 4.22(q, J=7Hz, 2H), 7.10(d, J=8Hz, 2H), 7.72(s, 1H), 7.84(d, J=8Hz, 2H) |
| 85 | MeO | MeO | Me | OH | MeO | —CH₂—(4-CN-C₆H₄) | OH | colorless oil | 2.04(s, 3H), 3.56(s, 2H), 3.68(s, 3H), 3.90(s, 3H), 3.98(s, 3H), 7.08(d, J=8Hz, 2H), 7.40(d, J=8Hz, 2H), 7.58(s, 1H) |
| 86 | EtO | EtO | Me | OH | EtO | —CH₂—(4-CN-C₆H₄) | OH | colorless oil | 1.28(t, J=7Hz, 3H), 1.38(t, J=7Hz, 3H), 1.40(t, J=7Hz, 3H), 2.06(s, 3H), 3.60(s, 2H), 3.88(q, J=7Hz, 2H), 4.08(q, J=7Hz, 2H), 4.12(q, J=7Hz, 2H), 7.06(d, J=8Hz, 2H), 7.36(d, J=8Hz, 2H), 7.58(s, 1H) |
| 87 | MeO | MeO | Me | OH | MeO | —CH₂—(2-F-C₆H₄) | OH | white solid 114–115° C. | 2.03(s, 3H), 3.60(s, 2H), 3.64(s, 3H), 3.86(s, 3H), 3.92(s, 3H), 6.77–7.13(m, 4H), 7.74(bs, 1H) |

TABLE 4-continued

Structure:
$$\text{R}^5\text{-C}_6\text{H}_2(\text{X})(\text{R}^3)(\text{R}^4)(\text{Y})\text{-CH=C(R}^1\text{)-C(=O)R}^2$$

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 88 | EtO | EtO | Me | OH | EtO | —CH₂—(2-F-C₆H₄) | OH | white solid 133–134° C. | 1.26(t, J=7Hz, 3H), 1.40(t, J=7Hz, 6H), 2.03(s, 3H), 3.63(bs, 2H), 3.83(q, J=7Hz, 2H), 4.09(q, J=7Hz, 2H), 4.21(q, J=7Hz, 2H), 6.80–7.14(m, 4H), 7.80 (bs, 1H) |
| 89 | MeO | MeO | Me | OH | MeO | —CH₂—(3-CF₃-C₆H₄) | OH | colorless oil | 2.00(s, 3H), 3.61(bs, 2H), 3.66(s, 3H), 3.89(s, 3H), 3.95(s, 3H), 7.13–7.37(m, 4H), 7.74(s, 1H) |
| 90 | EtO | EtO | Me | OH | EtO | —CH₂—(3-CF₃-C₆H₄) | OH | colorless oil | 1.27(t, J=7Hz, 3H), 1.37(t, J=7Hz, 3H), 1.39(t, J=7Hz, 3H), 2.01(s, 3H), 3.63(bs, 2H), 3.87(q, J=7Hz, 2H), 4.07(q, J=7Hz, 2H), 4.25(q, J=7Hz, 2H), 7.19–7.34 (m, 4H), 7.79(s, 1H) |
| 91 | MeO | MeO | Me | OH | MeO | —CH₂—(4-OMe-C₆H₄) | OH | white solid 138–140° C. | 2.08(s, 3H), 3.56(s, 2H), 3.64(s, 3H), 3.72(s, 3H), 3.88(s, 3H), 3.93(s, 3H), 6.64(d, J=10Hz, 2H), 6.90 (d, J=10Hz, 2H), 7.64(s, 1H) |
| 92 | EtO | EtO | Me | OH | EtO | —CH₂—(4-OMe-C₆H₄) | OH | white solid 130–132° C. | 1.24(t, J=7Hz, 3H), 1.36(t, J=7Hz, 6H), 2.02(s, 3H), 3.48(s, 2H), 3.70(s, 3H), 3.78(s, 3H), 4.04 (q, J=7Hz, 2H), 4.18(q, J=7Hz, 2H), 6.62(d, J=9Hz, 2H), 6.88(d, J=9Hz, 2H), 7.62(s, 1H) |
| 93 | MeO | MeO | Me | OH | MeO | —CH₂—(4-SMe-C₆H₄) | OH | light yellow oil | 2.06(s, 3H), 2.41(s, 3H), 3.53(bs, 2H), 3.64(s, 3H), 3.90(s, 6H), 6.94(d, J=8Hz, 2H), 7.09(d, J=8Hz, 2H), 7.71(bs, 1H) |

TABLE 4-continued

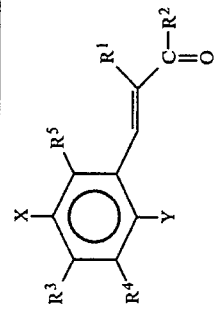

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 94 | MeO | MeO | Me | OH | MeO | -CH₂-⌬(OMe)(OMe) | OH | light yellow oil | 2.06(s, 3H), 3.46(s, 2H), 3.76(s, 3H), 3.78(s, 3H), 3.84(s, 3H), 3.88(s, 6H), 6.40-6.80(m, 3H), 7.48 (s, 1H) |
| 95 | MeO | EtO | Me | OH | MeO | -CH₂-⌬(OMe)(OMe) | OH | light yellow oil | 1.38(t, J=7Hz, 3H), 2.08(s, 3H), 3.46(s, 2H), 3.76 (s, 3H), 3.78(s, 3H), 3.84(s, 3H), 3.88(s, 3H), 1.0 (q, J=7Hz, 2H), 6.40-6.80(m, 3H), 7.48(s, 1H) |
| 96 | EtO | MeO | Me | OH | EtO | -CH₂-⌬(OMe)(OMe) | OH | light yellow oil | 1.28(t, J=7Hz, 3H), 1.38(t, J=7Hz, 3H), 2.08(s, 3H), 3.48(s, 2H), 3.76(s, 3H), 3.78(s, 3H), 3.84(s, 3H), 3.88(q, J=7Hz, 2H), 4.08(q, J=7Hz, 2H), 6.40-6.80 (m, 3H), 7.48(s, 1H) |
| 97 | EtO | EtO | Me | OH | EtO | -CH₂-⌬(OMe)(OMe) | OH | light yellow oil | 1.24(t, J=7Hz, 3H), 1.36(t, J=7Hz, 3H), 1.38(t, J= 7Hz, 3H), 2.08(s, 3H), 3.48(s, 2H), 3.76(s, 3H), 3.78(s, 3H), 3.88(q, J=7Hz, 2H), 4.08(q, J=7Hz, 2H), 4.12(q, J=7Hz, 2H), 6.40-6.80(m, 3H), 7.48(s, 1H) |
| 98 | MeO | MeO | MeO | MeO | OH | -CH₂-⌬(OMe)(OMe) | OH | brown oil | 3.54-3.97(m, 20H), 6.53-6.80(m, 3H), 7.64(s, 1H) |

TABLE 4-continued

Structure: Benzene ring with substituents X, Y, R³, R⁴, R⁵ and a vinyl group -C(R¹)=CH- connected to C(=O)-R²

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 99 | MeO | MeO | Me | OH | MeO | —CH₂—(phenyl with OEt, OEt) | OH | light yellow oil | 1.40(t, J=7Hz, 6H), 2.08(s, 3H), 3.54(s, 2H), 3.70 (s, 3H), 3.86(s, 3H), 3.88(s, 3H), 3.96(q, J=7Hz, 4H), 6.40–6.80(m, 3H), 7.58(s, 1H) |
| 100 | MeO | EtO | Me | OH | MeO | —CH₂—(phenyl with OEt, OEt) | OH | light yellow oil | 1.24(t, J=7Hz, 3H), 1.40(t, J=7Hz, 6H), 2.08(s, 3H), 3.54(s, 2H), 3.72(s, 3H), 3.84(s, 3H), 3.92(q, J=7Hz, 2H), 4.00(q, J=7Hz, 2H), 4.16(q, J=7Hz, 2H), 6.40–6.80(m, 3H), 7.48(s, 1H) |
| 101 | EtO | MeO | Me | OH | EtO | —CH₂—(phenyl with OEt, OEt) | OH | light yellow oil | 1.26(t, J=7Hz, 3H), 1.28(t, J=7Hz, 3H), 1.42(t, J=7Hz, 6H), 2.08(s, 3H), 3.46(s, 2H), 3.84(s, 3H), 3.88(q, J=7Hz, 2H), 3.92(q, J=7Hz, 2H), 3.98(q, J=7Hz, 2H), 4.10(q, J=7Hz, 2H), 6.40–6.80(m, 3H), 7.48(s, 1H) |
| 102 | EtO | EtO | Me | OH | EtO | —CH₂—(phenyl with OEt, OEt) | OH | light yellow oil | 1.28(t, J=7Hz, 3H), 1.38(t, J=7Hz, 6H), 1.39(t, J=7Hz, 6H), 2.04(s, 3H), 3.48(s, 2H), 3.82(t, J=7Hz, 2H), 3.92(t, J=7Hz, 2H), 3.98(t, J=7Hz, 4H), 4.18(t, J=7Hz, 2H), 6.40–6.80(m, 3H), 7.62(s, 1H) |
| 103 | MeO | MeO | Me | OH | MeO | —CH₂—(pyridyl) | OH | brown oil | 2.03(s, 3H), 3.59(bs, 2H), 3.66(s, 3H), 3.90(s, 3H), 3.96(s, 3H), 7.01–7.50(m, 2H), 7.69(s, 1H), 8.23–8.41(m, 2H) |
| 104 | MeO | MeO | Me | OH | MeO | —CH₂—(thienyl) | OH | white solid 98–100° C. | 2.06(s, 3H), 3.70(s, 3H), 3.74(s, 2H), 3.90(s, 6H), 6.60–7.10(m, 3H), 7.65(s, 1H) |

TABLE 4-continued

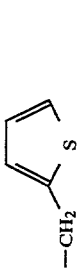

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 105 | MeO | EtO | Me | OH | MeO | —CH₂—(thiophene) | OH | white solid 101-102° C. | 1.38(t, J=7Hz, 3H), 2.06(s, 3H), 3.68(s, 3H), 3.72 (s, 2H), 3.88(s, 3H), 4.09(q, J=7Hz, 2H), 6.50-7.05 (m, 3H), 7.50(s, 1H) |
| 106 | EtO | MeO | Me | OH | EtO | —CH₂—(thiophene) | OH | white solid 140-142° C. | 1.28(t, J=7Hz, 3H), 1.38(t, J=7Hz, 3H), 2.08(s, 3H), 3.72(s, 2H), 3.84(q, J=7Hz, 2H), 3.88(s, 3H), 4.06 (q, J=7Hz, 2H), 6.50-7.00(m, 3H), 7.48(s, 1H) |
| 107 | EtO | EtO | Me | OH | EtO | —CH₂—(thiophene) | OH | white solid 101-103° C. | 1.30(t, J=7Hz, 3H), 1.38(t, J=7Hz, 6H), 2.08(s, 3H) 3.76(s, 2H), 3.86(q, J=7Hz, 2H), 4.12(q, J=7Hz, 4H) 6.40-7.05(m, 3H), 7.53(bs, 1H) |
| 108 | MeO | MeO | MeO | MeO | OH | —CH₂—(thiophene) | OH | brown oil | 3.60-3.74(m, 5H), 7.80(s, 3H), 3.86(s, 3H), 3.94 (s, 3H), 6.59-7.03(m, 3H), 7.66(s, 1H) |
| 109 | MeO | MeO | Me | OH | MeO | —CH₂—(5-Me-thiophene) | OH | colorless oil | 2.07(s, 3H), 2.34(s, 3H), 3.64(s, 5H), 3.89(s, 3H), 3.96(s, 3H), 6.30-6.50(m, 2H), 7.61(s, 1H) |
| 110 | MeO | MeO | Me | OH | MeO | —CH₂—(thiazole-Me) | OH | white solid 191-193° C. | 2.00(s, 3H), 2.57(s, 3H), 3.63(s, 5H), 3.84(s, 3H), 3.89(s, 3H), 6.57(s, 1H), 7.60(s, 1H) |
| 111 | MeO | MeO | Me | OH | MeO | —(phenyl) | OH | yellowish brown oil | 1.81(s, 3H), 3.64(s, 3H), 3.75(s, 3H), 3.92(s, 3H), 7.15(bs, 5H), 7.93(s, 1H) |

TABLE 4-continued

[Structure: phenyl ring with substituents X, R³, R⁴, R⁵, Y connected to C=C(R¹)-C(=O)-R²]

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 112 | MeO | MeO | Me | OH | MeO | —(CH₂)₂— | OH | colorless oil | 1.98(s, 3H), 2.36–2.86(m, 4H), 3.69(s, 3H), 2.92 (s, 3H), 3.97(s, 3H), 6.97–7.30(m, 5H), 7.64(s, 1H) |
| 113 | EtO | EtO | Me | OH | EtO | —(CH₂)₂— | OH | colorless oil | 1.27(t, 7Hz, 3H), 1.38(t, J=7Hz, 6H), 1.96(s, 3H), 2.31–2.91(m, 4H), 3.81(q, J=7Hz, 2H), 4.10(q, J=7Hz, 2H), 4.21(q, J=7Hz, 2H), 6.94–7.31(m, 5H), 7.63(S, 1H) |
| 114 | MeO | MeO | Me | OH | MeO | —(CH₂)₂— | OH | light yellow oil | 1.30–1.60(m, 4H), 2.03(s, 3H), 2.10–2.57(m, 4H), 3.61(s, 3H), 3.86(s, 3H), 3.94(s, 3H), 6.89–7.23 (m, 5H), 7.54(s, 1H) |
| 115 | EtO | EtO | Me | OH | EtO | —(CH₂)₄— | OH | brown oil | 1.06–1.57(m, 4H), 1.23(t, J=7Hz, 3H), 1.33(t, J=7Hz, 3H), 1.37(t, J=7Hz, 3H), 2.03(s, 3H), 2.06–2.60(m, 4H), 3.77(q, J=7Hz, 2H), 4.03(q, J=7Hz, 2H), 4.17(q, J=7Hz, 2H), 6.91–7.26(m, 5H), 7.54(s, 1H) |
| 116 | MeO | MeO | Me | OH | MeO | —(CH₂)₂O— | OH | brown oil | 2.07(s, 3H), 2.54–2.83(m, 2H), 3.66(s, 3H), 3.86 (s, 3H), 3.88–4.11(m, 2H), 3.94(s, 3H), 6.60–7.24 (m, 5H), 7.71(s, 1H) |
| 117 | MeO | MeO | Me | OH | MeO | —(CH₂)₃O— | OH | brown oil | 1.49–2.37(m, 4H), 2.06(s, 3H), 3.66(s, 3H), 3.83–3.91(m, 2H), 3.85(s, 3H), 3.94(s, 3H), 6.60–7.28 (m, 5H), 7.60(s, 1H) |

TABLE 4-continued

[Structure: phenyl ring with substituents R³, R⁴, R⁵, X, Y and a vinyl group =C(R¹)-C(=O)-R²]

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 118 | MeO | MeO | Me | OH | MeO | —(CH₂)₄O—[phenyl] | OH | brown oil | 1.54–1.77(m, 4H), 2.04(s, 3H), 2.06–2.31(m, 2H), 3.66(s, 3H), 3.66–3.97(m, 2H), 3.84(s, 3H), 3.93(s, 3H), 6.66–7.28(m, 5H), 7.56(s, 1H) |
| 119 | MeO | MeO | Me | OH | MeO | —(CH₂)₄O—[phenyl-OMe] | OH | light yellow oil | 1.48–1.71(m, 4H), 2.06(s, 3H), 2.11–2.37(m, 2H), 3.61–3.83(m, 2H), 3.66(s, 3H), 3.71(s, 3H), 3.84(s, 3H), 3.93(s, 3H), 6.71(s, 4H), 7.57(s, 1H) |
| 120 | MeO | MeO | Me | OH | MeO | —(CH₂)₆O—[phenyl] | OH | light yellow oil | 1.23–1.79(m, 8H), 2.04(s, 3H), 2.04–2.29(m, 2H), 3.64(s, 3H), 3.73–3.94(m, 2H), 3.86(s, 3H), 3.93(s, 3H), 6.74–7.30(m, 5H), 7.51(s, 1H) |
| 121 | MeO | MeO | Me | OH | MeO | —(CH₂)₃S—[phenyl] | OH | white solid 92° C. | 1.58–1.97(m, 2H), 2.04(s, 3H), 2.10–2.48(m, 2H), 2.78(t, J=7Hz, 2H), 3.63(s, 3H), 3.88(s, 3H), 3.94(s, 3H), 7.76(s, 5H), 7.58(s, 1H) |
| 122 | MeO | MeO | Me | OH | MeO | —(CH₂)₃SCH₂—[phenyl] | OH | white solid 84° C. | 1.50–1.90(m, 2H), 2.04(s, 3H), 2.08–2.40(m, 4H), 3.57(s, 2H), 3.65(s, 3H), 3.88(s, 3H), 3.95(s, 3H), 7.22(s, 5H), 7.61(s, 1H) |
| 123 | MeO | MeO | Me | OH | MeO | —(CH₂)₂O—[phenyl-OMe,OMe] | OH | light brown oil | 12.00(s, 3H), 2.37–2.71(m, 4H), 3.63(s, 3H), 3.74(s, 3H), 3.77(s, 3H), 3.86(s, 3H), 3.91(s, 3H), 6.43–6.70(m, 3H), 7.54(s, 1H) |

TABLE 4-continued

Structure:

R⁵, X on benzene ring with R³, R⁴, Y; substituent -C(R¹)=CH- attached to ring, with C=O-R² group

| Compd. No. | R³ | R⁴ | R⁵ | X | Y | R¹ | R² | Property, m.p. | ¹H-nuclear magnetic resonance spectrum δ value of TMS as internal reference (ppm) |
|---|---|---|---|---|---|---|---|---|---|
| 124 | MeO | MeO | Me | OH | MeO | —(CH₂)₇— (thiophene) | OH | colorless oil | 2.04(s, 3H), 2.40-2.67(m, 2H), 2.80-3.12(m, 2H), 3.66(s, 3H), 3.90(s, 3H), 3.97(s, 3H), 6.64(d, J=2.5Hz, 1H), 6.78(dd, J=2.5, 5Hz, 1H), 6.99(dd, J=1, 5Hz, 1H), 7.61(s, 1H) |
| 125 | MeO | EtO | Me | OH | OH | CH₃ CH₂CH₂CH—CH₃ | OH | colorless oil | 0.66(d, J=6Hz, 6H), 1.16-1.65(m, 3H), 1.38(t, J=7Hz, 3H), 2.08(s, 3H), 2.15-2.40(m, 2H), 3.88(s, 3H), 4.06(q, J=7Hz, 2H), 7.54(s, 1H) |
| 126 | MeO | MeO | Me | OH | OH | CH₃ CH₂CH₂CH—CH₃ | OH | colorless oil | 0.66(d, J=6Hz, 6H), 1.16-1.63(m, 3H), 2.14-2.43(m, 2H), 3.70(s, 3H), 3.87(s, 3H), 3.96(s, 3H), 7.54(s, 1H) |
| 127 | MeO | MeO | Me | OH | OH | —(CH₂)₈CH₃ | OH | white solid 79° C. | 0.86(t, J=6Hz, 3H), 1.10-1.60(m, 14H), 2.08(s, 3H), 2.06-2.36(m, 2H), 3.88(s, 3H), 3.92(s, 3H), 7.50(s, 1H) |
| 128 | MeO | MeO | Me | OH | OH | —CH₂— (thiophene) | OH | white solid 136° C. (decomp.) | 2.08(s, 3H), 3.74(s, 2H), 3.88(s, 3H), 3.90(s, 3H), 6.60-7.08(m, 3H), 7.65(s, 1H) |
| 129 | MeO | MeO | Me | OAc | OAc | —(CH₂)₈CH₃ | OH | colorless oil | 0.86(t, J=6Hz, 3H), 1.01-1.57(m, 14H), 1.98(s, 3H), 1.98-2.26(m, 2H), 2.22(s, 3H), 2.35(s, 3H), 3.81(s, 3H), 3.86(s, 3H), 7.31(s, 1H) |

TABLE 5

[Structure: cyclohexadienedione with R³, R⁴, R⁵ substituents and a =C(R¹)-C(=O)-R² side chain]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 130 | MeO | MeO | Me | Et | OH | orange solid 95–97° C. | 0.96(t, J=7Hz, 3H), 1.96(d, J=2Hz, 3H), 2.16(q, J=7Hz, 2H), 3.98(s, 3H), 4.02(s, 3H), 7.23(d, J=2Hz, 1H) |
| 131 | EtO | EtO | Me | Et | OH | orange solid 90–92° C. | 1.04(t, J=7Hz, 3H), 1.36(t, J=7Hz, 3H), 1.38(t, J=7Hz, 3H), 1.94(d, J=2Hz, 3H), 2.24(q, J=7Hz, 2H), 4.24(q, J=7Hz, 2H), 4.28(q, J=7Hz, 2H), 7.24(d, J=2Hz, 1H) |
| 132 | MeO | MeO | Me | -(CH₂)₇CH₃ | OH | orange solid 72–74° C. | 0.83(t, J=6Hz, 3H), 1.00–1.60(m, 6H), 1.96(d, J=2Hz, 3H), 1.90–2.20(m, 2H), 3.98(s, 3H), 4.02(s, 3H), 7.23(d, J=2Hz, 1H) |
| 133 | EtO | EtO | Me | -(CH₂)₇CH₃ | OH | orange solid 80–82° C. | 0.84(t, J=6Hz, 3H), 1.05–1.60(m, 6H), 1.31(t, J=7Hz, 3H), 1.33(t, J=7Hz, 3H), 1.98(d, J=2Hz, 3H), 1.95–2.20(m, 2H), 4.27(q, J=7Hz, 2H), 4.30(q, J=7Hz, 2H), 7.28(d, J=2Hz, 1H) |
| 134 | MeO | MeO | Me | -CH₂CH₂CH(CH₃)-CH₃ | OH | orange solid 82–84° C. | 0.83(t, J=6Hz, 6H), 1.10–1.40(m, 3H), 1.96(d, J=2Hz, 3H), 2.00–2.20(m, 2H), 3.98(s, 3H), 4.02(s, 3H), 7.23(d, J=2Hz, 1H) |
| 135 | MeO | EtO | Me | -CH₂CH₂CH(CH₃)-CH₃ | OH | orange solid 94–95° C. | 0.82(d, J=6Hz, 6H), 1.20–1.50(m, 3H), 1.40(t, J=7Hz, 3H), 1.97(d, J=2Hz, 3H), 2.00–2.20(m, 2H), 4.02(s, 3H), 4.20(q, J=7Hz, 2H), 7.22(d, J=2Hz, 1H) |
| 136 | EtO | MeO | Me | -CH₂CH₂CH(CH₃)-CH₃ | OH | orange solid 76–77° C. | 0.82(d, J=6Hz, 6H), 1.40(t, J=7Hz, 3H), 1.42(t, J=7Hz, 3H), 1.20–1.60(m, 3H), 1.98(d, J=2Hz, 3H), 1.90–2.20(m, 2H), 4.16(q, J=7Hz, 2H), 4.20(q, J=7Hz, 2H) |
| 137 | MeO | MeO | MeO | -CH₂CH₂CH(CH₃)-CH₃ | OH | orange solid 95–97° C. | 0.84(d, J=6Hz, 6H), 1.14–1.63(m, 3H), 2.01–2.30(m, 2H), 7.24(d, J=2Hz, 1H), 4.00(s, 3H), 4.02(s, 3H), 4.05(s, 3H), 7.27(s, 1H) |
| 138 | MeO | MeO | Me | cyclopentyl | OH | orange solid 116° C. | 1.37–1.93(m, 8H), 1.97(d, J=2Hz, 3H), 2.20–2.63(m, 1H), 3.99(s, 3H), 4.01(s, 3H), 7.13(s, 1H) |
| 139 | EtO | EtO | Me | cyclopentyl | OH | orange solid 108° C. | 1.39(t, J=7Hz, 3H), 1.40(t, J=7Hz, 3H), 1.50–1.90(m, 8H), 1.98(d, J=2Hz, 3H), 2.25–2.60(m, 1H), 4.29(q, J=7Hz, 2H), 4.31(q, J=7Hz, 2H), 7.19(s, 1H) |

TABLE 5-continued

Structure:

$$R^3, R^4, R^5 \text{ substituents on a quinone ring with } -CH=C(R^1)-C(=O)-R^2 \text{ side chain}$$

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 140 | MeO | MeO | Me | −CH₂−cyclopentyl | OH | orange solid 105–106° C. | 0.80–1.70(m, 9H), 1.96(d, J=2Hz, 3H), 2.00–2.20 (m, 2H), 3.96(s, 3H), 4.03(s, 3H), 7.26(d, J=2Hz, 1H) |
| 141 | MeO | MeO | Me | −CH₂−cyclohexyl | OH | orange solid 126–128° C. | 0.50–1.70(m, 11H), 1.94(d, J=2Hz, 3H), 1.90–2.10 (m, 2H), 3.96(s, 3H), 4.02(s, 3H), 7.28(d, J=2Hz, 1H) |
| 142 | MeO | EtO | Me | −CH₂−cyclohexyl | OH | orange solid 114–115° C. | 0.57–1.83(m, 11H), 1.37(t, J=7Hz, 3H), 1.93(d, J= 2Hz, 3H), 1.93–2.06(m, 2H), 4.04(s, 3H), 4.20(q, J= 7Hz, 2H), 7.31(bs, 1H) |
| 143 | EtO | MeO | Me | −CH₂−cyclohexyl | OH | yellowish orange solid 93° C. | 0.50–1.80(m, 11H), 1.40(t, J=7Hz, 3H), 1.90–2.10 (m, 2H), 1.96(d, J=2Hz, 3H), 3.99(s, 3H), 4.28(q, J= 7Hz, 2H), 7.31(bs, 1H) |
| 144 | EtO | EtO | Me | −CH₂−cyclohexyl | OH | orange solid 118–119° C. | 0.40–2.00(m, 11H), 1.38(t, J=7Hz, 3H), 1.39(t, J= 7Hz, 3H), 2.10(m, 2H), 2.16(s, 3H), 4.06(q, J=7Hz, 2H), 4.10(q, J=7Hz, 2H), 7.60(s, 1H) |
| 145 | MeO | n-PrO | Me | −CH₂−cyclohexyl | OH | orange solid 109–110° C. | 0.40–2.20(m, 18H), 1.93(d, J=2Hz, 3H), 4.03(s, 3H) 4.09(t, J=7Hz, 2H), 7.34(bs, 1H) |

TABLE 5-continued

[Structure: quinone ring with R³, R⁴ substituents, R⁵ and a vinyl group =CR¹-C(=O)-R²]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 146 | MeO | iso-PrO | Me | —CH₂—cyclohexyl | OH | orange solid 133–135° C. | 0.49–2.37(m, 13H), 1.31(d, J=6Hz, 6H), 1.94(d, J=2Hz, 3H), 4.03(s, 3H), 4.69(hept, J=6Hz, 1H), 7.34 (bs, 1H) |
| 147 | MeO | cyclohexyl-CH₂O | Me | —CH₂—cyclohexyl | OH | orange solid 107–109° C. | 0.57–2.11(m, 22H), 1.94(d, J=2Hz, 3H), 3.91(s, 2H), 3.97(s, 2H), 4.04(s, 3H), 7.37(bs, 1H) |
| 148 | MeO | H | MeO | —CH₂—cyclohexyl | OH | yellowish orange solid 116–117° C. | 0.43–1.77(m, 11H), 1.97–2.23(m, 2H), 3.83(s, 3H), 3.96(s, 3H), 5.83(s, 1H), 7.36(s, 1H) |
| 149 | MeO | MeO | MeO | —CH₂—cyclohexyl | OH | orange solid 94–95° C. | 0.43–1.79(m, 11H), 1.97–2.20(m, 2H), 3.96(s, 3H), 3.99(s, 3H), 4.01(s, 3H), 7.31(s, 1H) |
| 150 | MeO | MeO | Me | —(CH₂)₃—cyclohexyl | OH | orange solid 99–100° C. | 0.53–2.23(m, 17H), 1.96(d, J=2Hz, 3H), 3.97(s, 3H), 4.01(s, 3H), 7.24(bs, 1H) |
| 151 | MeO | MeO | Me | ─(CH₂)₇CH₃ | OH | orange solid 82–83° C. | 0.71–1.61(m, 15H), 1.90–2.26(m, 2H), 1.96(d, J=2Hz, 3H), 3.99(s, 3H), 4.01(s, 3H), 7.24(bs, 1H) |
| 152 | MeO | EtO | Me | ─(CH₂)₇CH₃ | OH | orange solid 49–50° C. | 0.67–1.60(m, 15H), 1.39(t, J=7Hz, 3H), 1.89–2.26 (m, 2H), 1.96(d, J=2Hz, 3H), 4.03(s, 3H), 4.21(q, J=7Hz, 2H), 7.23(bs, 1H) |
| 153 | MeO | EtO | Me | ─(CH₂)₇CH₃ | OH | orange solid 53° C. | 0.87(t, J=6Hz, 3H), 1.06–1.59(m, 14H), 1.39(t, J=7Hz, 3H), 1.96(d, J=2Hz, 3H), 1.96–2.21(m, 2H), 4.03(s, 3H), 4.22(q, J=7Hz, 2H), 7.21(bs, 1H) |
| 154 | EtO | MeO | Me | ─(CH₂)₈CH₃ | OH | orange solid 60° C. | 0.87(t, J=6Hz, 3H), 1.03–1.60(m, 14H), 1.40(t, J=7Hz, 3H), 1.96(d, J=2Hz, 3H), 1.96–2.22(m, 2H), |

TABLE 5-continued

[Structure: quinone with R¹, R², R³, R⁴, R⁵ substituents; C(=O)-R² group attached via vinyl]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 155 | EtO | EtO | Me | -(CH₂)₈CH₃ | OH | orange solid 51° C. | 0.87(t, J=6Hz, 3H), 1.02-1.57(m, 14H), 1.39(t, J=7Hz, 3H), 1.41(t, J=7Hz, 3H), 1.96(d, J=7Hz, 3H), 2.00-2.28(m, 2H), 4.23(q, J=7Hz, 2H), 4.31(q, J=7Hz, 2H), 7.27(bs, 1H) 3.99(s, 3H), 4.27(q, J=7Hz, 2H), 7.21(bs, 1H) |
| 156 | MeO | MeO | MeO | -(CH₂)₈CH₃ | OH | orange solid 67-68° C. | 0.69-1.63(m, 17H), 1.94-2.29(m, 2H), 3.97(s, 3H), 4.00(s, 3H), 4.03(s, 3H), 7.23(s, 1H) |
| 157 | MeO | MeO | Me | -(CH₂)₅C=C-CH₂CH₃ (H,H) | OH | orange solid 65° C. | 0.94(t, 7Hz, 3H), 1.08-1.60(m, 6H), 1.78-2.24(m, 6H), 1.96(d, J=2Hz, 3H), 3.97(s, 3H), 4.00(s, 3H), 5.16-5.40(m, 2H), 7.21(bs, 1H) |
| 158 | Meo | MeO | Me | -CH₂CH₂CH-CH₂)₇H (CH₃) | OH | orange solid 66-68° C. | 0.83(d, J=6Hz, 9H), 0.80-1.60(m, 10H), 1.97(d, J=2Hz, 3H), 1.85-2.20(m, 2H), 3.96(s, 3H), 4.00(s, 3H), 7.22(d, J=2Hz, 1H) |
| 159 | MeO | MeO | Me | -CH₂CH₂CH₂CCH₂CH₂CH=C(CH₃)CH₃ | OH | orange solid 50° C. | 0.86(d, J=6Hz, 3H), 1.00-1.50(m, 5H), 1.57(s, 3H), 1.67(s, 3H), 1.70-2.30(m, 4H), 1.97(d, J=2Hz, 3H), 3.98(s, 3H), 4.00(s, 3H), 4.85-5.12(m, 1H), 7.20 (bs, 1H) |
| 160 | MeO | MeO | Me | -(CH₂)₉CH₃ | OH | orange solid 61° C. | 0.88(t, J=6Hz, 3H), 1.09-1.60(m, 16H), 1.97(d, J=2Hz, 3H), 1.93-2.23(m, 2H), 3.98(s, 3H), 4.02(s, 3H), 7.21(bs, 1H) |
| 161 | MeO | MeO | Me | -(CH₂)₁₀CH₃ | OH | orange solid 69-70° C. | 0.88(t, J=6Hz, 3H), 1.09-1.60(m, 18H), 1.96(d, J=2Hz, 3H), 1.89-2.23(m, 2H), 3.97(s, 3H), 4.01(s, 3H), 7.23(bs, 1H) |
| 162 | MeO | MeO | Me | -(CH₂)₁₁CH₃ | OH | orange solid 75-76° C. | 0.88(t, J=6Hz, 3H), 1.09-1.66(m, 20H), 1.96(d, J=2Hz, 3H), 1.89-2.29(m, 2H), 3.99(s, 3H), 4.01(s, 3H), 7.24(bs, 1H) |
| 163 | MeO | MeO | Me | -(CH₂)₂C≡CH | OH | orange solid 112° C. | 1.52-1.92(m, 2H), 1.81(t, J=2Hz, 1H), 1.96-2.40 (m, 4H), 1.98(d, J=2Hz, 3H), 4.00(s, 6H), 7.36(bs, 1H) |
| 164 | MeO | EtO | Me | -(CH₂)₃C≡CH | OH | orange solid 114° C. | 1.39(t, J=7Hz, 3H), 1.52-1.78(m, 2H), 1.81(t, J=2Hz, 1H), 1.97(d, J=2Hz, 3H), 1.97-2.40(m, 4H), 4.00(s, 3H), 4.23(q, J=7Hz, 2H), 7.32(bs, 1H) |
| 165 | EtO | EtO | Me | -(CH₂)₃C≡CH | OH | yellowish orange solid 118° C. | 1.39(t, J=7Hz, 6H), 1.54-1.82(m, 2H), 1.81(t, J=2Hz, 1H), 1.97(t, J=2Hz, 3H), 1.93-2.41(m, 4H), 4.24(q, J=7Hz, 2H), 4.26(q, J=7Hz, 2H), 7.35(bs, 1H) |
| 166 | MeO | MeO | Me | -CH₂CN | OH | brown solid 78-80° C. | 2.00(s, 3H), 3.28(s, 2H), 3.96(s, 3H), 4.00(s, 3H), 7.44(bs, 1H) |

TABLE 5-continued

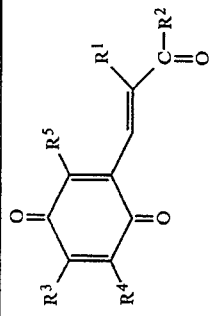

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 167 | EtO | EtO | Me | —CH₂CN | OH | brown oil | 1.32(t, J=7Hz, 3H), 1.38(t, J=7Hz, 3H), 1.98(s, 3H), 3.28(s, 2H), 4.22(q, J=7Hz, 2H), 4.28(q, J=7Hz, 2H), 7.48(s, 1H) |
| 168 | MeO | MeO | Me | ─(CH₂)₃CN | OH | orange solid 119–121° C. | 1.80–2.00(m, 2H), 1.96(d, J=2Hz, 3H), 2.00–2.40 (m, 4H), 3.98(s, 6H), 7.34(bs, 1H) |
| 169 | MeO | EtO | Me | ─(CH₂)₃CN | OH | orange solid 69–70° C. | 1.40(t, J=7Hz, 3H), 1.69–2.51(m, 6H), 1.99(d, J=2Hz, 3H), 4.03(s, 3H), 4.27(q, J=7Hz, 2H), 7.43(bs, 1H) |
| 170 | EtO | MeO | Me | ─(CH₂)₃CN | OH | orange solid 135° C. | 1.39(t, J=7Hz, 3H), 1.70–2.07(m, 2H), 1.97(d, J=2Hz, 2H), 2.12–2.40(m, 4H), 4.00(s, 3H), 4.27(q, J=7Hz, 2H), 7.38(bs, 1H) |
| 171 | EtO | EtO | Me | ─(CH₂)₃CN | OH | orange solid 107–108° C. | 1.40(t, J=7Hz, 3H), 1.42(t, J=7Hz, 3H), 1.70–2.07 (m, 2H), 1.97(d, J=2Hz, 3H), 2.00–2.40(m, 4H), 4.28 (q, J=7Hz, 2H), 4.32(q, J=7Hz, 2H), 7.32(bs, 1H) |
| 172 | MeO | nPrO | Me | ─(CH₂)₃CN | OH | orange solid 95–97° C. | 1.00(t, J=7Hz, 3H), 1.60–2.46(m, 8H), 1.96(d, J=2Hz, 3H), 3.99(s, 3H), 4.13(t, J=6Hz, 2H), 7.39(bs, 1H) |
| 173 | MeO | iso-PrO | Me | ─(CH₂)₃CN | OH | yellow solid 99–100° C. | 1.33(d, J=6Hz, 6H), 1.59–2.46(m, 6H), 1.97(d, J=2Hz, 3H), 4.00(s, 3H), 4.69(hept, 6Hz, 1H), 7.37 (bs, 1H) |
| 174 | MeO | n-OctO | Me | ─(CH₂)₃CN | OH | red oil | 0.88(t, J=6Hz, 3H), 1.22–1.58(m, 10H), 1.58–1.95 (m, 4H), 1.97(d, J=2Hz, 3H), 2.12–2.42(m, 4H), 4.00 (s, 3H), 4.15(t, J=7Hz, 2H), 7.36(bs, 1H) |
| 175 | MeO | H | MeO | ─(CH₂)₃CN | OH | orange solid 124–126° C. | 1.67–2.47(m, 6H), 3.80(s, 3H), 3.97(s, 3H), 5.86 (s, 1H), 7.20(s, 1H) |
| 176 | MeO | MeO | Me | ─(CH₂)₇CN | OH | yellowish orange solid 96–98° C. | 1.40–1.80(m, 4H), 1.98(d, J=2Hz, 3H), 2.00–2.40 (m, 4H), 3.98(s, 3H), 4.02(s, 3H), 7.28(bs, 1H) |
| 177 | MeO | EtO | Me | ─(CH₂)₇CN | OH | orange solid 106–108° C. | 1.36(t, J=7Hz, 3H), 1.39–1.67(m, 4H), 1.93(bs, 3H), 1.94–2.36(m, 4H), 4.00(t, J=7Hz, 3H), 4.19(q, J=7Hz, 2H), 7.17(bs, 1H) |
| 178 | EtO | MeO | Me | ─(CH₂)₇CN | OH | orange solid 99–102° C. | 1.39(t, J=7Hz, 3H), 1.41–1.65(m, 4H), 1.93(bs, 3H), 1.91–2.37(m, 4H), 3.97(s, 3H), 4.23(q, J=7Hz, 2H), 7.20(bs, 1H) |
| 179 | EtO | EtO | Me | ─(CH₂)₇CN | OH | orange solid 80–82° C. | 1.40(t, J=7Hz, 3H), 1.42(t, J=7Hz, 3H), 1.50–1.80 (m, 4H), 1.98(d, J=2Hz, 3H), 2.00–2.40(m, 4H), 4.28 (q, J=7Hz, 2H), 4.32(q, J=7Hz, 2H), 7.32(bs, 1H) |
| 180 | MeO | MeO | MeO | ─(CH₂)₇CN | OH | brown solid 111–112° C. | 1.40–1.81(m, 4H), 2.00–2.46(m, 4H), 3.97(s, 3H), 4.04(s, 6H), 7.27(s, 1H) |
| 181 | MeO | MeO | Me | ─(CH₂)₈CN | OH | yellowish orange solid 57° C. | 1.08–1.80(m, 12H), 1.97(d, J=2Hz, 3H), 2.00–2.43 (m, 4H), 2.98(s, 3H), 4.01(s, 3H), 7.23(bs, 1H) |

TABLE 5-continued

![Structure: quinone with R3, R4 at bottom, R5 at top, and substituent -CH=C(R1)-C(=O)-R2]

| Compd. No. | R3 | R4 | R5 | R1 | R2 | Property, m.p. | 1H-nuclear magnetic resonance spectrum δ value of TMS as internal reference (ppm) |
|---|---|---|---|---|---|---|---|
| 182 | EtO | EtO | Me | ‑(CH₂)₈CN | OH | orange solid 86° C. | 1.07–1.80(m, 12H), 1.38(t, J=7Hz, 3H), 1.39(t, J=7Hz, 3H), 1.96(d, J=2Hz, 3H), 1.96–2.42(m, 4H), 4.23(q, J=7Hz, 2H), 4.28(q, J=7Hz, 2H), 7.22(bs, 1H) |
| 183 | MeO | MeO | Me | ‑(CH₂)₃SMe | OH | orange solid 78–80° C. | 1.60–1.90(m, 2H), 1.96(d, J=2Hz, 3H), 2.00(s, 3H), 2.15–2.50(m, 4H), 3.98(s, 3H), 4.00(s, 3H), 7.30 (d, J=2Hz, 1H) |
| 184 | MeO | EtO | Me | ‑(CH₂)₃S‑Me | OH | orange solid 74–76° C. | 1.40(t, J=7Hz, 3H), 1.63–1.89(m, 2H), 1.97(d, J=2Hz, 3H), 2.00(s, 3H), 2.19–2.49(m, 4H), 4.03(s, 3H), 4.25(q, J=7Hz, 2H), 7.34(bs, 1H) |
| 185 | MeO | MeO | MeO | ‑(CH₂)₃S‑Me | OH | orange solid 61–62° C. | 1.61–1.93(m, 2H), 2.00(s, 3H), 2.14–2.47(m, 4H), 3.97(s, 3H), 4.01(s, 3H), 4.03(s, 3H), 7.29(s, 1H) |
| 186 | MeO | MeO | Me | ‑(CH₂)₃S‑cyclohexyl | OH | orange solid 64–66° C. | 1.10–2.00(m, 12H), 1.97(d, J=2Hz, 3H), 2.10–2.50 (m, 5H), 4.00(s, 6H), 7.30(bs, 1H) |
| 187 | MeO | EtO | Me | ‑(CH₂)₃S‑cyclohexyl | OH | orange oil | 1.39(t, J=7Hz, 3H), 1.05–1.49(m, 4H), 1.49–2.04 (m, 7H), 1.94(d, J=2Hz, 3H), 2.11–2.60(m, 6H), 4.00 (s, 3H), 4.23(q, J=7Hz, 2H), 7.29(bs, 1H) |
| 188 | MeO | MeO | MeO | ‑(CH₂)₃S‑cyclohexyl | OH | brown oil | 1.00–2.04(m, 12H), 2.13–2.69(m, 5H), 3.96(s, 3H), 4.00(s, 3H), 4.01(s, 3H), 7.27(bs, 1H) |
| 189 | MeO | MeO | Me | ‑CH₂‑(tetrahydropyran-2-yl) | OH | orange oil | 0.80–1.86(m, 6H), 1.94(d, J=2Hz, 3H), 2.17–2.37 (m, 2H), 3.09–3.63(m, 2H), 3.66–3.86(m, 1H), 3.97 (s, 3H), 4.00(s, 3H), 7.31(bs, 1H) |
| 190 | MeO | MeO | Me | ‑(CH₂CH₂O)₃Me | OH | red oil | 1.96(d, J=2Hz, 3H), 2.29–2.51(m, 2H), 3.34(s, 3H), 3.40–3.66(m, 10H), 3.98(s, 3H), 4.00(s, 3H), 7.23 (bs, 1H) |

TABLE 5-continued

Structure:

$$\text{R}^3, \text{R}^4, \text{R}^5 \text{ substituted benzoquinone with } -CR^1=CR^1-C(=O)-R^2 \text{ side chain}$$

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 191 | MeO | MeO | Me | —CH₂—(C₆H₅) | OH | orange solid 111–113° C. | 1.96(d, J=2Hz, 3H), 3.52(s, 2H), 3.95(s, 6H), 6.90–7.20(m, 5H), 7.36(bs, 1H) |
| 192 | EtO | EtO | Me | —CH₂—(C₆H₅) | OH | red oil | 1.34(t, J=7Hz, 3H), 1.35(t, J=7Hz, 3H), 1.78(s, 3H), 3.48(s, 2H), 4.12(q, J=7Hz, 2H), 4.16(q, J=7Hz, 2H), 6.80–7.20(m, 5H), 7.26(s, 1H) |
| 193 | MeO | MeO | Me | —CH₂—(4-F-C₆H₄) | OH | orange solid 133–134° C. | 1.90(d, J=2Hz, 3H), 3.46(s, 2H), 3.94(s, 6H), 6.60–7.05(m, 4H), 7.36(bs, 1H) |
| 194 | MeO | EtO | Me | —CH₂—(4-F-C₆H₄) | OH | orange solid 79–80° C. | 1.40(t, J=7Hz, 3H), 1.90(d, J=2Hz, 3H), 3.47(bs, 2H), 3.97(s, 3H), 4.19(q, J=7Hz, 2H), 6.71–7.06(m, 4H), 7.39(bs, 1H) |
| 195 | EtO | EtO | Me | —CH₂—(4-F-C₆H₄) | OH | orange solid 108–110° C. | 1.38(t, J=7Hz, 3H), 1.39(t, J=7Hz, 3H), 1.92(t, J=7Hz, 3H), 3.48(s, 2H), 4.20(q, J=7Hz, 2H), 4.22(q, J=7Hz, 2H), 6.60–7.10(m, 4H), 7.36(bs, 1H) |
| 196 | MeO | MeO | Me | —CH₂—(4-CO₂H-C₆H₄) | OH | orange solid 180° C. (decomp.) | 1.96(d, J=2Hz, 3H), 3.70(s, 2H), 3.98(s, 6H), 7.20(d, J=8Hz, 2H), 7.38(bs, 1H), 7.86(d, J=8Hz, 2H) |

TABLE 5-continued

[Structure: quinone ring with R³, R⁴, R⁵ substituents and a =CH-C(R¹)=C(R²)=O side chain]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 197 | EtO | EtO | Me | —CH₂—C₆H₄—CO₂H (para) | OH | orange solid 200° C. (decomp.) | 1.42(t, 7Hz, 6H), 1.96(d, J=2Hz, 3H), 3.70(s, 2H), 4.26(q, J=7Hz, 2H), 4.30(q, J=7Hz, 2H), 7.26(d, J=8Hz, 2H), 7.38(bs, 1H), 7.90(d, J=8Hz, 2H) |
| 198 | MeO | MeO | Me | —CH₂—C₆H₄—CN (para) | OH | orange solid 152–153° C. | 1.94(d, J=2Hz, 3H), 3.50(s, 2H), 3.98(s, 3H), 3.40 (s, 3H), 7.10(d, J=8Hz, 2H), 7.38(bs, 1H), 7.42(d, J=8Hz, 2H) |
| 199 | EtO | EtO | Me | —CH₂—C₆H₄—CN (para) | OH | orange solid 124–126° C. | 1.40(t, J=7Hz, 3H), 1.42(t, J=7Hz, 3H), 1.94(d, J= 2Hz, 3H), 3.60(s, 2H), 4.18(q, J=7Hz, 2H), 4.22(q, J=7Hz, 2H), 7.04(d, J=8Hz, 2H), 7.34(d, J=8Hz, 2H), 7.38(bs, 1H) |
| 200 | MeO | MeO | Me | —CH₂—C₆H₄—F (ortho) | OH | orange oil | 2.03(d, J=2Hz, 3H), 3.54(s, 2H), 3.94(s, 3H), 3.96 (s, 3H), 6.77–7.46(m, 4H), 7.74(bs, 1H) |
| 201 | EtO | EtO | Me | —CH₂—C₆H₄—F (ortho) | OH | brown oil | 1.34(t, J=7Hz, 3H), 1.36(t, J=7Hz, 3H), 1.84(d, J= 2Hz, 3H), 3.54(bs, 2H), 4.19(q, J=7Hz, 2H), 4.23(q, J=7Hz, 2H), 6.69–7.23(m, 4H), 7.40(bs, 1H) |
| 202 | MeO | MeO | Me | —CH₂—C₆H₄—CF₃ (meta) | OH | orange solid 152–155° C. | 1.89(d, J=2Hz, 3H), 3.57(bs, 2H), 3.96(s, 3H), 3.97 (s, 3H), 7.17–7.51(m, 5H) |

TABLE 5-continued

[Structure: quinone ring with R³, R⁴ on one side, R⁵ and substituent —C(R¹)=CH— connected to C(=O)—R² at top]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 203 | EtO | EtO | Me | —CH₂—(C₆H₄-CF₃) | OH | orange solid 85–89° C. | 1.34(t, J=7Hz, 3H), 1.37(t, J=7Hz, 3H), 1.86(d, J=2Hz, 3H), 3.54(bs, 2H), 4.17(q, J=7Hz, 2H), 4.21(q, J=7Hz, 2H), 7.17–7.54(m, 5H) |
| 204 | MeO | MeO | Me | —CH₂—(C₆H₄-OMe) | OH | orange solid 98–100° C. | 1.90(d, J=2Hz, 3H), 3.46(s, 2H), 3.70(s, 3H), 3.96(s, 6H), 6.66(d, J=10Hz, 2H), 6.90(d, J=10Hz, 2H), 7.40(bs, 1H) |
| 205 | EtO | EtO | Me | —CH₂—(C₆H₄-OMe) | OH | yellowish orange solid 88–90° C. | 1.36(t, J=7Hz, 6H), 1.90(t, J=2Hz, 3H), 3.46(s, 2H), 3.70(s, 3H), 4.20(q, J=7Hz, 2H), 4.21(q, J=7Hz, 2H), 6.66(q, J=9Hz, 2H), 6.90(d, J=9Hz, 2H), 7.35(bs, 1H) |
| 206 | MeO | MeO | Me | —CH₂—(C₆H₄-SMe) | OH | orange solid 119–121° C. | 1.89(d, J=2Hz, 3H), 2.40(s, 3H), 3.49(bs, 2H), 3.97(s, 6H), 6.91(d, J=8Hz, 2H), 7.09(d, J=8Hz, 2H), 7.40(bs, 1H) |
| 207 | MeO | MeO | Me | —CH₂—(C₆H₃(OMe)₂) | OH | orange oil | 1.84(d, J=2Hz, 3H), 3.52(s, 2H), 3.70(s, 3H), 3.74(s, 3H), 3.88(s, 6H), 6.40–6.80(m, 3H), 7.12(bs, 1H) |
| 208 | MeO | EtO | Me | —CH₂—(C₆H₃(OMe)₂) | OH | orange oil | 1.32(t, J=7Hz, 3H), 1.84(d, J=2Hz, 3H), 3.52(s, 2H), 3.70(s, 6H), 3.88(s, 3H), 4.12(q, J=7Hz, 2H), 6.40–6.80(m, 3H), 7.12(bs, 1H) |

TABLE 5-continued

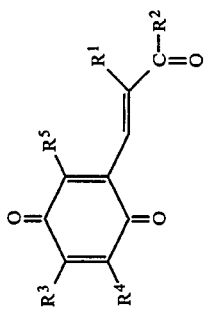

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 209 | EtO | MeO | Me | —CH₂—⟨C₆H₃(OMe)(OMe)⟩ | OH | orange oil | 1.32(t, J=7Hz, 3H), 1.82(t, J=2Hz, 3H), 3.48(s, 2H) 3.68(s, 6H), 3.88(s, 3H), 4.10(q, J=7Hz, 2H), 6.40–6.80(m, 3H), 7.18(bs, 1H) |
| 210 | EtO | EtO | Me | —CH₂—⟨C₆H₃(OMe)(OMe)⟩ | OH | orange oil | 1.34(t, J=7Hz, 3H), 1.36(t, J=7Hz, 3H), 1.86(d, J=2H, 3H), 3.47(s, 2H), 3.74(s, 6H), 4.12(q, J=7Hz, 2H), 4.14(q, J=7Hz, 2H), 6.40–6.80(m, 3H), 7.36 (bs, 1H) |
| 211 | MeO | MeO | MeO | —CH₂—⟨C₆H₃(OMe)(OMe)⟩ | OH | orange oil | 3.40–3.60(m, 2H), 3.77(bs, 6H), 3.89(s, 3H), 3.94 (s, 3H), 3.96(s, 3H), 6.37–6.74(m, 3H), 7.37(s, 1H) |
| 212 | MeO | MeO | Me | —CH₂—⟨C₆H₃(OEt)(OMe)⟩ | OH | orange solid 101–103° C. | 1.38(t, J=7Hz, 6H), 1.88(d, J=2Hz, 3H), 3.56(s, 2H), 3.94(s, 6H), 3.96(q, J=7Hz, 4H), 6.40–6.80(m, 3H), 7.36(bs, 1H) |
| 213 | MeO | EtO | Me | —CH₂—⟨C₆H₃(OEt)(OMe)⟩ | OH | orange oil | 1.36(t, J=7Hz, 6H), 1.38(t, J=7Hz, 3H), 1.84(d, J=2Hz, 3H), 3.48(s, 2H), 3.92(s, 3H), 3.94(q, J=7Hz, 4H), 4.13(q, J=7Hz, 2H), 6.40–6.80(m, 3H), 7.24 (bs, 1H) |

TABLE 5-continued

![structure: quinone with R3, R4 on ring, R5, and substituent =C(R1)-C(=O)-R2]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 214 | EtO | MeO | Me | —CH₂—(3,4-diethoxyphenyl) | OH | orange oil | 1.36(t, J=7Hz, 9H), 1.83(d, J=2Hz, 3H), 3.46(s, 2H), 3.92(s, 3H), 3.93(q, J=7Hz, 4H), 4.10(q, J=7Hz, 2H), 6.40–6.80(m, 3H), 7.20(bs, 1H) |
| 215 | EtO | EtO | Me | —CH₂—(3,4-diethoxyphenyl) | OH | orange solid 90–92° C. | 1.37(t, J=7Hz, 3H), 1.38(t, J=7Hz, 3H), 1.39(t, J=7Hz, 3H), 1.40(t, J=7Hz, 3H), 1.88(d, J=2Hz, 3H), 3.44(s, 2H), 3.95(q, J=7Hz, 4H), 4.16(q, J=7Hz, 2H), 4.18(q, J=7Hz, 2H), 6.40–6.80(m, 3H), 7.36(bs, 1H) |
| 216 | MeO | MeO | Me | —CH₂—(pyridin-3-yl) | OH | reddish orange solid 164° C. (decomp.) | 1.80(bs, 3H), 3.44(bs, 2H), 3.87(s, 3H), 3.90(s, 3H), 7.06–7.50(m, 3H), 8.16–8.37(m, 2H) |
| 217 | MeO | MeO | Me | —CH₂—(thiophen-2-yl) | OH | red oil | 1.54(d, J=2Hz, 3H), 3.72(s, 2H), 3.99(s, 6H), 6.60–7.10(m, 3H), 7.40(bs, 1H) |
| 218 | MeO | EtO | Me | —CH₂—(thiophen-2-yl) | OH | red oil | 1.38(t, J=7Hz, 3H), 1.94(d, J=2Hz, 3H), 3.72(s, 2H), 3.98(s, 3H), 4.20(q, J=7Hz, 2H), 6.50–7.05(m, 3H), 7.38(bs, 1H) |
| 219 | EtO | MeO | Me | —CH₂—(thiophen-2-yl) | OH | orange solid 110–112° C. | 1.38(t, J=7Hz, 3H), 1.96(d, J=2Hz, 3H), 3.72(s, 2H), 3.98(s, 3H), 4.18(q, J=7Hz, 2H), 6.50–7.00(m, 3H), 7.30(bs, 1H) |
| 220 | EtO | EtO | Me | —CH₂—(thiophen-2-yl) | OH | red oil | 1.38(t, J=7Hz, 6H), 1.92(d, J=2Hz, 3H), 3.72(s, 2H), 4.22(q, J=7Hz, 4H), 6.60–7.05(m, 3H), 7.38(bs, 1H) |

TABLE 5-continued

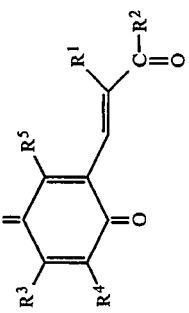

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 221 | MeO | MeO | MeO | —CH₂-(2-thienyl) | OH | brown oil | 3.57–3.86(m, 2H), 3.93(s, 6H), 3.99(s, 3H), 6.53–7.09(m, 2H), 7.21(bs, 1H), 7.27–7.46(m, 1H) |
| 222 | MeO | MeO | Me | —CH₂-(5-methyl-2-thienyl) | OH | red oil | 1.92(d, J=2Hz, 3H), 2.34(s, 3H), 3.61(s, 2H), 3.99 (s, 6H), 6.32–6.52(m, 2H), 7.32(bs, 1H) |
| 223 | MeO | MeO | Me | —CH₂-(2-methyl-4-thiazolyl) | OH | orange solid 132–134° C. | 1.76(d, J=2Hz, 3H), 2.47(s, 3H), 3.50(s, 2H), 3.86 (s, 6H), 6.84(s, 1H), 7.09–7.15(bs, 1H) |
| 224 | MeO | MeO | Me | —CH₂-tolyl | OH | orange solid 140–145° C. | 1.70(d, J=2Hz, 3H), 3.74(s, 3H), 3.94(s, 3H), 6.97–7.33(m, 5H), 7.56(bs, 1H) |
| 225 | MeO | MeO | Me | —(CH₂)₂-phenyl | OH | orange solid 117–119° C. | 1.83(d, J=2Hz, 3H), 2.29–2.91(m, 4H), 3.99(s, 3H), 4.00(s, 3H), 6.97–7.34(m, 6H) |
| 226 | EtO | EtO | Me | —(CH₂)₂-phenyl | OH | orange solid 107–108° C. | 1.39(t, J=7Hz, 3H), 1.40(t, J=7Hz, 3H), 1.83(d, J=2Hz, 3H), 2.31–2.63(m, 2H), 2.63–2.89(m, 2H), 4.23 (q, J=7Hz, 2H), 4.27(q, J=7Hz, 2H), 7.00–7.37(m, 6H) |
| 227 | MeO | MeO | Me | —(CH₂)₃-phenyl | OH | yellowish orange solid 95–97° C. | 1.31–1.61(m, 4H), 1.91(d, J=2Hz, 3H), 1.97–2.25 (m, 2H), 2.36–2.66(m, 2H), 3.91(s, 3H), 4.01(s, 3H), 6.94–7.33(m, 6H) |

TABLE 5-continued

![Structure: cyclohexadienedione with R3, R4, R5 substituents and a =CH-C(R1)=C(-R2)(=O) group shown as R5, R3, R4 on ring and R1, C-R2, =O on side chain]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 228 | EtO | EtO | Me | ⁺(CH₂)₄⁻ phenyl | OH | yellowish orange solid 77–78° C. | 1.24–1.59(m, 4H), 1.33(t, J=7Hz, 3H), 1.39(t, J=7Hz, 3H), 1.93(d, J=2Hz, 3H), 2.00–2.24(m, 2H), 2.34–2.62(m, 2H), 4.23(q, J=7Hz, 2H), 4.27(q, J=7Hz, 2H), 7.00–7.37(m, 6H) |
| 229 | MeO | MeO | Me | ⁺(CH₂)₂⁻O-phenyl | OH | orange solid 110–111° C. | 2.00(s, 3H), 2.46-2.74(m, 2H), 3.84-4.14(m, 2H), 3.94(s, 3H), 3.96(s, 3H), 6.60-7.27(m, 5H), 7.39 (bs, 1H) |
| 230 | MeO | MeO | Me | ⁺(CH₂)₃⁻O-phenyl | OH | red oil | 1.80-2.14(m, 2H), 1.91(d, J=2Hz, 3H), 2.21-2.50 (m, 2H), 3.69-3.94(m, 2H), 3.83(s, 3H), 3.93(s, 3H), 6.60-7.40(m, 6H) |
| 231 | MeO | MeO | Me | ⁺(CH₂)₄⁻O-phenyl | OH | orange solid 71–74° C. | 1.51-1.78(m, 4H), 1.94(d, J=2Hz, 3H), 2.00-2.29 (m, 2H), 3.69-4.03(m, 2H), 3.93(s, 3H), 3.97(s, 3H), 6.66-7.40(m, 6H) |
| 232 | MeO | MeO | Me | ⁺(CH₂)₄⁻O-(4-OMe-phenyl) | OH | orange solid 121–122° C. | 1.49-1.74(m, 4H), 1.94(d, J=2Hz, 3H), 2.03-2.31 (m, 2H), 3.69-3.86(m, 2H), 3.71(s, 3H), 3.93(s, 3H), 3.96(s, 3H), 6.71(s, 4H), 7.23(bs, 1H) |
| 233 | MeO | MeO | Me | ⁺(CH₂)₆⁻O-phenyl | OH | orange solid 84–85° C. | 1.16-1.86(m, 8H), 1.94(d, J=2Hz, 3H), 1.86-2.30 (m, 2H), 3.70-4.10(m, 2H), 3.96(s, 3H), 4.00(s, 3H), 6.74-7.31(m, 6H) |

TABLE 5-continued

![Structure: quinone with R3, R4, R5 substituents and side chain -C(R1)=CH- connecting to C(=O)-R2]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 234 | MeO | MeO | Me | -(CH₂)₃-S-C₆H₅ | OH | yellowish orange solid 75° C. | 1.58–2.00(m, 2H), 1.90(d, J=2Hz, 3H), 2.10–2.50 (m, 2H), 2.80(t, J=7Hz, 2H), 3.91(s, 3H), 3.99(s, 3H), 7.13(s, 5H), 7.26(bs, 1H) |
| 235 | MeO | MeO | Me | -(CH₂)₃-SCH₂-C₆H₅ | OH | red oil | 1.54–1.90(m, 2H), 1.93(d, J=2Hz, 3H), 2.06–2.41 (m, 4H), 3.58(s, 2H), 3.97(s, 3H), 3.98(s, 3H), 7.21 (s, 5H), 7.28(bs, 1H) |
| 236 | MeO | MeO | Me | -(CH₂)₂-(2-OMe,4-OMe-C₆H₃) | OH | orange solid 149–151° C. | 1.80((d, J=2Hz, 3H), 2.34–2.80(m, 4H), 3.77(s, 6H) 3.96(s, 3H), 3.97(s, 3H), 6.46–6.69(m, 3H), 7.26 (bs, 1H) |
| 237 | MeO | MeO | Me | -(CH₂)₂-(2-thienyl) | OH | orange solid 80° C. | 1.88(d, J=2Hz, 3H), 2.36–2.68(m, 2H), 2.87–3.20 (m, 2H), 3.99(s, 3H), 4.00(s, 3H), 6.68(d, J=2.5Hz, 1H), 6.80(dd, 2.5, 5Hz, 1H), 7.02(dd, J=1, 5Hz, 1H), 7.29(bs, 1H) |
| 238 | MeO | MeO | Me | -(CH₂)₇-CH₃ | -N(nPr)H | orange solid 55–56° C. | 0.86(t, J=6Hz, 3H), 0.96(t, J=7Hz, 3H), 1.00–1.50 (m, 14H), 1.40–1.80(m, 2H), 1.94(d, J=2Hz, 3H), 2.00–2.20(m, 2H), 3.20–3.50(m, 2H), 3.96(s, 3H), 3.98(s, 3H), 5.90(bs, 1H) |
| 239 | MeO | MeO | Me | -(CH₂)₇-CH₃ | -N(Et)₂ | red oil | 0.86(t, J=6Hz, 3H), 1.00–1.50(m, 20H), 1.96(d, J= 2Hz, 3H), 2.00–2.20(m, 2H), 3.40–3.70(m, 4H), 3.98(s, 6H) |
| 240 | MeO | MeO | Me | -(CH₂)₇-CH₃ | -N(piperidine) | red oil | 0.86(t, J=6Hz, 3H), 1.00–1.50(m, 14H), 1.50–1.80 (m, 6H), 1.94(d, J=2Hz, 3H), 2.00–2.20(m, 2H), 3.50–3.80(m, 4H), 3.96(s, 6H), 5.86(bs, 1H) |

TABLE 5-continued

[Structure: quinone ring with R³, R⁴, R⁵ substituents and side chain CR¹=CH- connected to C(=O)-R²]

| Compd. No. | R³ | R⁴ | R⁵ | R¹ | R² | Property, m.p. | ¹H-nuclear magnetic resonance spectrum δ value of TMS as internal reference (ppm) |
|---|---|---|---|---|---|---|---|
| 241 | MeO | MeO | Me | $-(CH_2)_8CH_3$ | —N(piperidin-1-yl)—4-OH | colorless oil | 0.86(t, J=6Hz, 3H), 1.00–1.50(m, 14H), 1.50–2.00 (m, 4H), 1.94(d, J=2Hz, 3H), 2.00–2.20(m, 2H), 3.10–3.50(m, 4H), 3.96(s, 6H), 3.90–4.20(m, 1H), 5.88 (bs, 1H) |
| 242 | MeO | MeO | Me | $-(CH_2)_8CH_3$ | —NH-cyclohexyl | orange solid 85–86° C. | 0.86(t, J=6Hz, 3H), 1.00–1.50(m, 14H), 1.20–2.00 (m, 10H), 1.94(d, J=2Hz, 3H), 2.00–2.20(m, 2H), 3.60–3.90(m, 1H), 3.88(s, 6H), 6.76(s, 1H) |
| 243 | MeO | MeO | Me | $-(CH_2)_8CH_3$ | —NCH₂CH₂OH H | red oil | 0.86(t, J=6Hz, 3H), 1.00–1.50(m, 14H), 1.94(d, J= 2Hz, 3H), 2.00–2.20(m, 2H), 3.30–3.60(m, 2H), 3.60–3.85(m, 2H), 3.94(s, 3H), 3.98(s, 3H), 6.42(bs, 1H) |
| 244 | MeO | MeO | Me | $-(CH_2)_8CH_3$ | —NH—C₆H₄—OMe | red oil | 0.86(t, J=6Hz, 3H), 1.00–1.50(m, 14H), 1.96(d, J= 2Hz, 3H), 2.00–2.20(m, 2H), 3.76(s, 3H), 3.96(s, 3H), 4.00(s, 3H), 6.52(bs, 1H), 6.85(d, J=9Hz, 2H), 7.48(d, J=9Hz, 2H) |
| 245 | MeO | MeO | Me | $-(CH_2)_8CH_3$ | —NH-thiazol-2-yl | red oil | 0.86(t, J=6Hz, 3H), 1.00–1.60(m, 14H), 1.96(d, J= 2Hz, 3H), 2.10–2.40(m, 2H), 3.98(s, 3H), 4.00(s, 3H), 6.76(bs, 1H), 6.94(d, J=4Hz, 1H), 7.42(d, J= 4Hz, 1H) |
| 246 | MeO | MeO | Me | $-(CH_2)_8CH_3$ | OEt | red oil | 0.86(t, J=6Hz, 3H), 1.05–1.50(m, 14H), 1.33(t, J= 7Hz, 3H), 1.94(d, J=2Hz, 3H), 1.93–2.20(m, 2H), 3.98(s, 3H), 4.01(s, 3H), 4.23(q, J=7Hz, 2H), 7.07 (bs, 1H) |

We claim:

1. A quinone derivative represented by the formula:

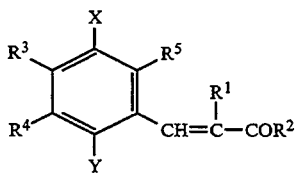

wherein X and Y may be the same or different from each other and each represents a hydroxyl group or a group represented by the formula —(—OCH$_2$—)$_n$—OR$^6$, where n is 0 or 1 and R$^6$ is a lower alkyl group or an acyl group; R$^1$ is an alkyl group having 2 to 20 carbon atoms; a cycloalkyl group; a cycloalkylalkyl group; an alkenyl group; an alkynyl group; an arylalkyl group; a group represented by the formula —(—CH$_2$—)$_p$—CN where p is an integer from 1 to 10; an alkyl-substituted heteroaryl group, a group represented by the formula —(—CH$_2$—)$_q$—B where q is an integer from 1 to 6 and B is a group of the formula

where r is 0, 1 or 2 and R$^7$ is a lower alkyl group, a cycloalkyl group or an aryl group, a group represented by the formula —O—R$^{11}$ where R$^{11}$ is a lower alkyl group or an aryl group, or a group represented by the formula —(—CH$_2$—CH$_2$—O—)$_s$—CH$_3$ where s is an integer from 1 to 3; R$^2$ is a group represented by —OR$^8$ where R$^8$ is a hydrogen atom, a lower alkyl group, or a group represented by the formula

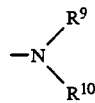

where R$^9$ and R$^{10}$ is the same or different from each other and each is a hydrogen atom, a lower alkyl group, a hydroxyalkyl group or a heteroaryl group, or R$^9$ and R$^{10}$ form a heterocyclic group with the adjacent nitrogen atom, said heterocyclic group optionally being substituted; and R$^3$, R$^4$ and R$^5$ are the same or different from each other and each is a hydrogen atom, a lower alkyl group or a lower alkoxy group or a pharmacologically acceptable salt thereof.

2. A quinone derivative or a pharmacologically acceptable salt thereof according to claim 1, wherein R$^1$ is an alkyl group having 2 to 20 carbon atoms and R$^2$ is a group represented by the formula —OR$^8$ wherein R$^8$ is a hydrogen atom or a lower alkyl group, or a group represented by the formula:

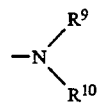

wherein R$^9$ and R$^{10}$ may be the same or different from each other and each is a hydrogen atom, a lower alkyl group, a hydroxyalkyl group or a heteroaryl group, or R$^9$ and R$^{10}$ form a ring together with the nitrogen atom bonded thereto, which may further contain a nitrogen atom and/or an oxygen atom and may be substituted.

3. A quinone derivative or a pharmacologically acceptable salt thereof according to claim 2, wherein R$^2$ is a hydroxyl group.

4. A quinone derivative or a pharmacologically acceptable salt thereof according to claim 1, wherein R$^1$ is an alkyl group having 2 to 12 carbon atoms and R$^2$ is a hydroxyl group.

5. A quinone derivative or a pharmacologically acceptable salt thereof according to claim 1, wherein R$^1$ is an alkyl group having 7 to 12 carbon atoms and R$^2$ is a hydroxyl group.

6. A quinone derivative or a pharmacologically acceptable salt thereof according to claim 1, wherein R$^1$ is a nonyl group.

7. A quinone derivative or a pharmacologically acceptable salt thereof according to claim 1, wherein R$^1$ is a nonyl group and R$^2$ is a hydroxyl group.

8. A quinone derivative or a pharmacologically acceptable salt thereof according to claim 1, wherein R$^1$ is a 3-methylbutyl group.

9. A quinone derivative or a pharmacologically acceptable salt thereof according to claim 1, wherein R$^1$ is a cycloalkyl group.

10. A quinone derivative or a pharmacologically acceptable salt thereof according to claim 1, wherein the cycloalkylalkyl group is a cyclohexylmethyl group.

11. A quinone derivative or a pharmacologically acceptable salt thereof according to claim 1, wherein R$^3$, R$^4$ and R$^5$ are each independently a lower alkyl group or a lower alkoxy group.

12. A quinone derivative or a pharmacologically acceptable salt thereof according to claim 1, wherein R$^3$ and R$^4$ are each a lower alkoxy group and R$^5$ is a lower alkyl group.

13. A quinone derivative or a pharmacologically acceptable salt thereof according to claim 1, wherein R$^3$ and R$^4$ are each a methoxy group and R$^5$ is a methyl group.

14. A quinone derivative or a pharmacologically acceptable salt thereof according to claim 1, wherein R$^3$ and R$^4$ are each a methoxy group, R$^5$ is a methyl group, R$^1$ is a nonyl group and R$^2$ is a hydroxyl group.

15. A quinone derivative or a pharmacologically acceptable salt thereof according to claim 1, wherein R$^3$, R$^4$ and R$^5$ are each a methoxy group, R$^2$ is a hydroxyl group and R$^1$ is a 3-methylbutyl group.

16. A quinone derivative or a pharmacologically acceptable salt thereof according to claim 1, wherein R$^3$ is a methoxy group, R$^4$ is an ethoxy group, R$^5$ is a methyl group, R$^1$ is a 3-methylbutyl group and R$^2$ is a hydroxyl group.

17. A quinone derivative or a pharmacologically acceptable salt thereof according to claim 1, wherein R$^3$ is a methoxy group, R$^4$ is an ethoxy group, R$^5$ is a methyl group, R$^1$ is a cyclohexylmethyl group and R$^2$ is a hydroxyl group.

18. A quinone derivative or a pharmacologically acceptable salt thereof according to claim 1, wherein R$^3$ and R$^4$ are each a methoxy group, R$^5$ is a methyl group, R$^1$ is a nonyl group and R$^2$ is a hydroxyl group.

19. A pharmacological composition which comprises a pharmacologically effective amount of the quinone derivative or a salt thereof as defined in claim 1 and a pharmacologically acceptable carrier.

* * * * *